(12) United States Patent
Goldman et al.

(10) Patent No.: US 7,576,065 B2
(45) Date of Patent: Aug. 18, 2009

(54) ENHANCING NEUROTROPHIN-INDUCED NEUROGENESIS BY ENDOGENOUS NEURAL PROGENITOR CELLS BY CONCURRENT OVEREXPRESSION OF BRAIN DERIVED NEUROTROPHIC FACTOR AND AN INHIBITOR OF A PRO-GLIOGENIC BONE MORPHOGENETIC PROTEIN

(75) Inventors: Steven A. Goldman, South Salem, NY (US); Eva Chmielnicki, New York, NY (US); Aris Economides, Tarrytown, NY (US)

(73) Assignees: Cornell Research Foundation, Inc., Ithaca, NY (US); Regeneron Pharmaceuticals, Tarrytown, NY (US)

( * ) Notice: Subject to any disclaimer, the term of this patent is extended or adjusted under 35 U.S.C. 154(b) by 135 days.

(21) Appl. No.: 10/368,809

(22) Filed: Feb. 14, 2003

(65) Prior Publication Data

US 2003/0199447 A1    Oct. 23, 2003

Related U.S. Application Data

(60) Provisional application No. 60/358,005, filed on Feb. 15, 2002.

(51) Int. Cl.
*A61K 48/00* (2006.01)
*C12N 15/63* (2006.01)

(52) U.S. Cl. .................................... 514/44; 435/320.1
(58) Field of Classification Search ................. 514/44; 435/320.1
See application file for complete search history.

(56) References Cited

U.S. PATENT DOCUMENTS

| | | | |
|---|---|---|---|
| 5,082,670 A | 1/1992 | Gage et al. | |
| 5,196,315 A | 3/1993 | Ronnett et al. | |
| 5,308,763 A | 5/1994 | Ronnett et al. | |
| 5,453,361 A | 9/1995 | Yancopoulos et al. | |
| 5,491,084 A | 2/1996 | Chalfie et al. | |
| 5,654,189 A | 8/1997 | Lee et al. | |
| 5,661,032 A | 8/1997 | Miller et al. | |
| 5,750,376 A | 5/1998 | Weiss et al. | |
| 5,753,505 A | 5/1998 | Luskin | |
| 5,753,506 A | 5/1998 | Johe | |
| 5,766,948 A | 6/1998 | Gage et al. | |
| 5,770,414 A | 6/1998 | Gage et al. | |
| 5,780,300 A | 7/1998 | Artavanis-Tsakonas et al. | |
| 5,830,858 A | 11/1998 | Rosenthal | |
| 5,837,535 A | 11/1998 | Joseph et al. | |
| 5,851,832 A | 12/1998 | Weiss et al. | |
| 5,874,304 A | 2/1999 | Zolotukhin et al. | |
| 5,958,767 A | 9/1999 | Snyder et al. | |
| 5,968,829 A | 10/1999 | Carpenter | |
| 5,980,885 A | 11/1999 | Weiss et al. | |
| 6,000,772 A | 12/1999 | Miller et al. | |
| 6,071,889 A | 6/2000 | Weiss et al. | |
| 6,075,007 A | 6/2000 | Economides et al. | |
| 6,225,122 B1 | 5/2001 | Sah et al. | |
| 6,245,564 B1 | 6/2001 | Goldman et al. | |
| 6,251,669 B1 | 6/2001 | Luskin | |
| 2001/0024827 A1 | 9/2001 | Luskin | |

FOREIGN PATENT DOCUMENTS

| | | |
|---|---|---|
| WO | WO 93/01275 | 1/1993 |
| WO | WO 94/02593 | 2/1994 |
| WO | WO 96/38541 | 5/1996 |
| WO | WO 96/38576 | 12/1996 |
| WO | WO 97/07200 | 2/1997 |
| WO | WO 98/32879 | 7/1998 |
| WO | WO 99/29279 | 6/1999 |
| WO | WO 99/49014 | 9/1999 |
| WO | WO 00/23571 | 4/2000 |
| WO | WO 01/46384 A2 | 6/2001 |
| WO | WO 01/53503 A1 | 7/2001 |

OTHER PUBLICATIONS

Benraiss A. et al. 2001. Journal of Neuroscience 21:6718-6731.*
Akaneya Y. et al. 1997. Journal of Neuroscience 17:6707-6716.*

(Continued)

*Primary Examiner*—Deborah Crouch
*Assistant Examiner*—David Montanari
(74) *Attorney, Agent, or Firm*—Nixon Peabody LLP

(57) ABSTRACT

The present invention relates to a method of inducing neuronal production in a subject, a method of recruiting neurons to a subject's brain, and a method of treating a neurodegenerative condition by administering a neurotrophic factor and an inhibitor of pro-gliogenic bone morphogenetic proteins. Also disclosed is a method of suppressing astrocyte generation and inducing neuronal production in a subject, a method of treating a neurologic condition, and a method of suppressing glial scar formation in a subject by administering an inhibitor of pro-gliogenic bone morphogenetic proteins. Finally, the present invention involves a method of introducing a heterogeneous protein into a subject's brain and spinal cord by introducing a nucleic acid molecule encoding the heterogeneous protein introduced into the subject's ependyma, permitting the protein from the nucleic acid molecule to be expressed within the subject's ependyma, and permitting the expressed protein to migrate within the subject's brain and spinal cord.

26 Claims, 8 Drawing Sheets

OTHER PUBLICATIONS

Lim DA, Noggin antagonizes BMP signaling to create a niche for adult neurogenesis, 2000, Neuron, vol. 28, pp. 713-726.*

Concalves M, A concise peer into the background, initial thoughts, and practices of human gene therapy, 2005, BioEssays, vol. 27, pp. 506-517.*

Verma IM, Gene Therapy: Twenty-first century medicine, 2005, Annu. Rev. Biochem. vol. 74, pp. 711-738.*

Parekh-Olmedo H, Gene therapy progress and prospects: targeted gene repair, 2005, Gene Therapy, vol. 12, pp. 639-646.*

High K, Gene transfer for hemophilia: can therapeutic efficacy in large animals be safely translated to patients?, 2005, J. Thrombosis and Haemostasis, vol. 3, pp. 1682-1691.*

Ellinwood et al., Gene therapy for lysosomal storage diseases: the lessons and promise of animal models, 2004, J. Gene Medicine, vol. 6, pp. 481-506.*

Shekhar C., Gene therapy trial on hold, Jul. 31, 2007.*

Mastakov et al., 2002, J. Virology, vol. 76, No. 16, pp. 8446-8454.*

Lo et al., 1999, Human Gene Therapy, vol. 10, pp. 201-213.*

Schubert et al., 2008, Molecular Therapy, vol. 16, No. 4, pp. 640-646.*

Faulkner et al., 2005, J Neuroscience, vol. 24(9), pp. 2143-2155.*

Trendenelburg et al., 2005, Glia, vol. 51, pp. 307-320.*

Chen et al., "Transgenic Animals with Inducible, Targeted Gene Expression in Brain," *Molecular Pharmacology* 54:495-503 (1998).

Kalcheim et al., "Neurotrophin 3 is a Mitogen for Cultured Neural Crest Cells," *Proc. Natl. Acad. Sci. USA* 89:1661-1665 (1992).

Pixley et al., "Effects of Insulin-Like Growth Factor 1 on Olfactory Neurogenesis In Vivo and In Vitro," *Annals of the New York Academy of Sciences* 855:244-247 (1998).

Frade et al., "Insulin-Like Growth Factor-I Stimulates Neurogenesis in Chick Retina by Regulating Expression of the α6 Integrin Subunit," *Development* 122:2497-2506 (1996).

Gage et al., "Isolation, Characterization, and Use of Stem Cells From the CNS," *Annu. Rev. Neurosci.* 18:159-192 (1995).

Gage et al., "Survival and Differentiation of Adult Neuronal Progenitor Cells Transplanted to the Adult Brain," *Proc. Natl. Acad. Sci. USA* 92:11879-11883 (1995).

Gao et al., "Neurotrophin-4/5 (NT-4/5) and Brain-Derived Neurotrophic Factor (BDNF) Act at Later Stages of Cerebellar Granule Cell Differentiation," *J. Neurosci.* 15(4):2656-2667 (1995).

Memberg et al., "Proliferation, Differentiation, and Survival of Rat Sensory Neuron Precursors In Vitro Require Specific Trophic Factors," *Mol. Cell. Neurosci.* 6:323-335 (1995).

Hoshimaru et al., "Differentiation of the Immortalized Adult Neuronal Progenitor Cell Line HC2S2 into Neurons by Regulatable Suppression of the v-myc Oncogene," *Proc. Natl. Acad. Sci. USA* 93:1518-1523 (1996).

Ockel et al., "In Vivo Effects of Neurotrophin-3 During Sensory Neurogenesis," *Development* 122:301-307 (1996).

Gravel et al., "Adenoviral Gene Transfer of Ciliary Neurotrophic Factor and Brain-Derived Neurotrophic Factor Leads to Long Term Survival of Axotomized Motor Neurons," *Nature Medicine* 3:765-770 (1997).

Ribotta et al., "Prevention of Motoneuron Death by Adenovirus-Mediated Neurotrophic Factors," *J. Neurosci. Res.* 48:281-285 (1997).

DiPolo et al., "Prolonged Delivery of Brain-Derived Neurotrophic Factor by Adenovirus-Infected Müller Cells Temporarily Rescues Injured Retinal Ganglion Cells," *Proc. Nat'l. Acad. Sci. USA* 95:3978-3983 (1998).

Fariñas et al., "Characterization of Neurotrophin and Trk Receptor Functions in Developing Sensory Ganglia: Direct NT-3 Activation of TrkB Neurons In Vivo," *Neuron* 21:325-334 (1998).

Fukumitsu et al., "Simultaneous Expression of Brain-Derived Neurotrophic Factor and Neurotrophin-3 in Cajal-Retzius, Subplate and Ventricular Progenitor Cells During Early Development Stages of the Rat Cerebral Cortex," *Neurosci.* 84(1):115-127(1998).

Kempermann et al., "New Nerve Cells for the Adult Brain. Adult Neurogenesis and Stem Cell Concept in Neurological Research," *Nervenarzt* 69(10):851-857 (1998) (English abstract).

Isenmann et al., "Excess Target-Derived Brain-Derived Neurotrophic Factor Preserves the Transient Uncrossed Retinal Projection to the Superior Colliculus," *Mol. Cell. Neurosci.* 14:52-65 (1999).

Kukekov et al., "Multipotent Stem/Progenitor Cells with Similar Properties Arise from Two Neurogenic Regions of Adult Human Brain," *Experimental Neurology* 156:333-344 (1999).

Takahashi et al., "Retinoic Acid and Neurotrophins Collaborate to Regulate Neurogenesis in Adult-Derived Neural Stem Cell Cultures," *J. Neurobiology* 38:65-81 (1999).

Zaheer et al., "Enhanced Expression of Neurotrophic Factors by C6 Rat Glioma Cells After Transfection with Glia Maturation Factor," *Neuroscience Letters* 265:203-206 (1999).

Ahmed et al., "BDNF Enhances the Differentiation but Not the Survival of CNS Stem Cell-Derived Neuronal Precursors," *J. Neurosci.* 15(8):5765-5778 (1995).

Alvarez-Buylla et al., "Neuronal Stem Cells in the Brain of Adult Vertebrates," *Stem Cells* 13:263-72 (1995).

Bajocchi et al., "Direct In Vivo Gene Transfer to Ependymal Cells in the Central Nervous System Using Recombinant Adenovirus Vectors," *Nature Genetics* 3:229-234 (1993).

Craig et al., "In Vivo Growth Factor Expansion of Endogenous Subependymal Neural Precursor Cell Populations in the Adult Mouse Brain," *J. Neurosci.* 16(8):2649-2658 (1996).

Driesse et al., "Intra-CSF Administered Recombinant Adenovirus Causes an Immune Response-Mediated Toxicity," *Gene Therapy* 7:1401-1409 (2000).

Goldman et al., "Neuronal Precursors of the Adult Rat Subependymal Zone Persist into Senescence, With No Decline in Spatial Extent or Response to BDNF," *J. Neurobiology* 32:554-566 (1997).

Goldman et al., "Neural Precursors and Neuronal Production in the Adult Mammalian Forebrain," *Ann. N.Y. Acad. Sci.* 835: 30-55 (1997).

Goldman et al., "Strategies Utilized by Migrating Neurons of the Postnatal Vertebrate Forebrain," *Trends in Neurosciences* 21(3):107-114 (1998).

Goldman et al., "In Vitro Neurogenesis by Neuronal Precursor Cells Derived from the Adult Songbird Brain," *J. Neurosci.* 12(7):2532-2541 (1992).

Gould et al., "Neurogenesis in the Neocortex of Adult Primates," *Science* 286:548-552 (1999).

Guan et al., "Selective Neuroprotective Effects with Insulin-Like Growth Factor-1 in Phenotypic Striatal Neurons Following Ischemic Brain Injury In Fetal Sheep," *Neuroscience* 95(3):831-839 (2000).

Ivkovic et al., "Expression of the Striatal DARPP-32/ARPP-21 Phenotype in GABAergic Neurons Requires Neurotrophins In Vivo and In Vitro," *J. Neurosci.* 19(13):5409-5419 (1999).

Kaplan, "Proliferation of Subependymal Cells in the Adult Primate CNS: Differential Uptake of DNA-Labeled Precursors," *J. Hirnforsch* 23:23-33 (1983).

Kirschenbaum et al., "Brain-derived Neurotrophic Factor Promotes the Survival of Neurons Arising From the Adult Rat Forebrain Subependymal Zone," *Proc. Nat'l. Acad. Sci.* 92:210-214 (1995).

Kuhn et al., "Epidermal Growth Factor and Fibroblast Growth Factor-2 Have Different Effects on Neural Progenitors in the Adult Rat Brain," *J. Neurosci.* 17(15):5820-5829 (1997).

Leventhal et al., "Endothelial Trophic Support of Neuronal Production and Recruitment from the Adult Mammalian Subependyma," *Molec. Cell. Neurosci.* 13:450-464 (1999).

Lindsay et al., "Neurotrophic Factors: From Molecule to Man," *Trends in Neurosciences* 17(5):182-190 (1994).

Lois et al., "Chain Migration of Neuronal Precursors," *Science* 271:978-981 (1996).

Magavi et al., "Induction of Neurogenesis in the Neocortex of Adult Mice," *Nature* 405:951-955 (2000).

Menezes et al., "The Division of Neuronal Progenitor Cells During Migration in the Neonatal Mammalian Forebrain," *Mol. Cell. Neurosci.* 6:496-508 (1995).

Mizisin et al., "BDNF Attenuates Functional and Structural Disorders in Nerves of Galactose-fed Rats," *J. Neuropathol. & Exp. Neurol.* 56:1290-1301 (1997).

Palmer et al., "Fibroblast Growth Factor-2 Activates a Latent Neurogenic Program in Neural Stem Cells from Diverse Regions of the Adult CNS," *J. Neurosci.* 19(19):8487-8497 (1999).
Palmer et al., "FGF-2-Responsive Neuronal Progenitors Reside in Proliferative and Quiescent Regions of the Adult Rodent Brain," *Mol. Cell. Neurosci.* 6:474-486 (1995).
Pencea et al., "Infusion of BDNF Into the Lateral Ventricle of the Adult Rat Leads to an Increase in the Number of Newly Generated Cells in the Fore, Mid and Hindbrain Parenchyma," *Soc. Neurosci.* 25:2045 (1999) (Abstract only).
Reynolds et al, "Generation of Neurons and Astrocytes from Isolated Cells of the Adult Mammalian Central Nervous System," *Science* 255:1707-1710 (1992).
Richards et al., "De Novo Generation of Neuronal Cells from the Adult Mouse Brain," *Proc. Nat'l. Acad. Sci.* 89:8591-8595(1992).
Roy et al., "Identification, Isolation, and Promoter-Defined Separation of Mitotic Oligodendrocyte Progenitor Cells from the Adult Human Subcortical White Matter," *J. Neurosci.* 19(22):9986-9995 (1999).
Roy et al., "In Vitro Neurogenesis by Progenitor Cells Isolated from the Adult Human Hippocampus," *Nature Medicine* 6(3):271-277 (2000).
Vescovi et al., "bFGF Regulates the Proliferative Fate of Unipotent (Neuronal) and Bipotent (Neuronal/Astroglial) EGF-Generated CNS Progenitor Cells," *Neuron* 11:951-966 (1993).
Wang et al., "Cortical Interneurons Upregulate Neurotrophins In Vivo in Response to Targeted Apoptotic Degeneration of Neighboring Pyramidal Neurons," *Exp. Neurol.* 154:389-402 (1998).
Wang et al., "Isolation of Neuronal Precursors by Sorting Embryonic Forebrain Transfected Regulated by the T α 1 Tubulin Promoter," *Nat. Biotechnol.* 16(2):196-201 (1998).
Yoon et al., "Adenovirus-Mediated Gene Delivery into Neuronal Precursors of the Adult Mouse Brain," *Proc. Nat'l. Acad. Sci.* 93:11974-11979 (1996).
Zigova et al., "Intraventricular Administration of BDNF Increases the Number of Newly Generated Neurons in the Adult Olfactory Bulb," *Mol. Cell. Neurosci.* 11:234-245 (1998).
McDonald et al., "A Structural Superfamily of Growth Factors Containing a Cystine Knot Motif," *Cell* 73:421-424 (1993).
Lim et al., "Noggin Antagonizes BMP Signaling to Create a Niche for Adult Neurogenesis," *Neuron* 28:713-726 (2000).
Zimmerman et al., "The Spemann Organizer Signal noggin Binds and Inactivates Bone Morphogenetic Protein 4," *Cell* 86: 599-606 (1996).
Gritti et al., "Multipotential Stem Cells from the Adult Mouse Brain Proliferate and Self-Renew in Response to Basic Fibroblast Growth Factor," *J. Neurosci.* 16:1091-1100 (1996).
Gloster et al., "The Tα 1 α-Tubulin Promoter Specifies Gene Expression as a Function of Neuronal Growth and Regeneration in Transgenic Mice," *J. Neurosci.* 14(12):7319-7330 (1994).
Lothian et al., "An Evolutionarily Conserved Region in the Second Intron of the Human Nestin Gene Directs Gene Expression to CNS Progenitor Cells and to Early Neural Crest Cells," *Eur. J. Neurosci.* 9:452-462 (1997).
Weiss et al., "Is There a Neural Stem Cell in the Mammalian Forebrain?", *TINS* 19:387-393 (1996).
Gould et al., "Proliferation of Granule Cell Precursors in the Dentate Gyrus of Adult Monkeys is Diminished by Stress," *Proc. Natl. Acad. Sci. USA* 95:3168-3171 (1998).
Eriksson et al., "Neurogenesis in the Adult Human Hippocampus," *Nature Medicine* 4:1313-1317 (1998).
Pincus et al., "Neural Stem and Progenitor Cells: A Strategy for Gene Therapy and Brain Repair," *Neurosurgery* 42(4):858-867 (1998).
Roy et al., "Promoter-Targeted Selection and Isolation of Neural Progenitor Cells From the Adult Human Ventricular Zone," *J. Neurosci. Res.* 59:321-331 (2000).
Brüstle et al., "Chimeric Brains Generated by Intraventricular Transplantation of Fetal Human Brain Cells Into Embryonic Rats," *Nature Biotech.* 16:1040-1044 (1998).
Flax et al., "Engraftable Human Neural Stem Cells Respond to Developmental Cues, Replace Neurons, and Express Foreign Genes," *Nature Biotech.* 16:1033-1039 (1998).

Frederiksen et al., "Proliferation and Differentiation of Rat Neuroepithelial Precursor Cells In Vivo," *J. Neurosci.* 8:1144-1151 (1988).
Fricker et al., "Site-Specific Migration and Neuronal Differentiation of Human Neural Progenitor Cells After Transplantation In the Adult Rat Brain," *J. Neurosci.* 19:5990-6005 (1999).
Menezes et al., "Expression of Neuron-Specific Tubulin Defines a Novel Population in the Proliferative Layers of the Developing Telencephalon," *J. Neurosci.* 14:5399-5416 (1994).
Miller et al., "Isotypes of α-Tubulin are Differentially Regulated During Neuronal Maturation," *J. Cell Biology* 105(No. 6, Pt. 2):3065-3073 (1987).
Miller et al., "Rapid Induction of the Major Embryonic α-Tubulin mRNA, Tα1, During Nerve Regeneration in Adult Rats," *J. Neurosci.* 9:1452-1463 (1989).
Morshead et al., "Neural Stem Cells in the Adult Mammalian Forebrain: A Relatively Quiescent Subpopulation of Subependymal Cells," *Neuron* 13:1071-1082 (1994).
Pincus et al., "Fibroblast Growth Factor-2/Brain-Derived Neurotrophic Factor-Associated Maturation of New Neurons Generated from Adult Human Subependymal Cells," *Ann. Neurology* 43:576-585 (1998).
Sakakibara et al., "Mouse-Musashi-1, a Neural RNA-Binding Protein Highly Enriched in the Mammalian CNS Stem Cell," *Dev. Biol.* 176:230-242 (1996).
Sakakibara et al., "Expression of Neural RNA-Binding Proteins in the Postnatal CNS: Implications of Their Roles in Neuronal and Glial Cell Development," *J. Neurosci.* 17(21):8300-8312 (1997).
Svendsen et al., "Long-Term Survival of Human Central Nervous System Progenitor Cells Transplanted into a Rat Model of Parkinson's Disease," *Exp. Neurol.* 148:135-146 (1997).
Uchida et al., "Direct Isolation of Huamn Central Nervous System Stem Cells," *Proc. Natl. Acad. Sci.* 97(26):14720-14725 (2000).
Vescovi et al, "Isolation and Cloning of Multipotential Stem Cells From the Embryonic Human CNS and Establishment of Transplantable Human Stem Cells Lines by Epigenetic Stimulation," *Exp. Neurol.* 156:71-83 (1999).
Wang et al., "Promoter-Based Isolation and Fluorescence-Activated Sorting of Mitotic Neuronal Progenitor Cells From the Adult Mammalian Ependymal/Subependymal Zone," *Dev. Neurosci.* 22:167-176 (2000).
Barami et al., "Hu Protein as an Early Marker of Neuronal Phenotypic Differentiation by Subependymal Zone Cells of the Adult Songbird Forebrain," *J. Neurobiol.* 28(1):82-101 (1995).
Rossant et al., "Expression of a Retinoic Acid Response Element-hsplacZ Transgene Defines Specific Domains of Transcriptional Activity During Mouse Embryogenesis," *Genes Dev.* 5:1333-1344 (1991).
Graham et al., "Manipulation of Adenovirus Vector," *Methods of Molecular Biology: Gene Transfer and Expression Protocols*, E. Murray, ed. The Humana Press, Clifton, NJ, pp. 109-128 (1991).
Anderson et al., "A Bipotential Neuroendocrine Precursor Whose Choice of Cell Fate is Determined by NGF and Glucocorticoids," *Cell* 47:1079-1090 (1986).
Barres et al., "A Crucial Role for Neurotrophin-3 in Oligodendrocyte Development," *Nature* 367:371-375 (1994).
Dahlstrand et al., "Characterization of the Human Nestin Gene Reveals a Close Evolutionary Relationship to Neurofilaments," *J. Cell Sci.* 103:589-597 (1992).
DiCicco-Bloom et al., "NT-3 Stimulates Sympathetic Neuroblast Proliferation by Promoting Precursor Survival," *Neuron* 11:1101-1111 (1993).
Goldman, "Adult Neurogenesis: From Canaries to the Clinic," *J. Neurobiol.* 36:267-286 (1998).
Lu et al., "A Paradigm for Distinguishing the Roles of Mitogenesis and Trophism in Neuronal Precursor Proliferation," *Dev. Brain Res.* 94:31-36 (1996).
Sieber-Blum, "Role of the Neurotrophic Factors BDNF and NGF in the Commitment of Pluripotent Neural Crest Cells," *Neuron* 6:949-955 (1991).
Weiss et al., "Multipotent CNS Stem Cells are Present in the Adult Mammalian Spinal Cord and Ventricular Neuroaxis," *J. Neurosci.* 16(23):7599-7609 (1996).

Pencea et al., "Infusion of Brain-Derived Neurotrophic Factor into the Lateral Ventricle of the Adult Rat Leads to New Neurons in the Parenchyma of the Striatum, Septum, Thalamus, and Hypothalamus," *J. of Neuroscience* 21(17):6706-6717 (2001).

Benraiss et al., "In Vivo Transduction of the Adult Rat Ventricular Zone with an Adenoviral BDNF Vector Increases Neuronal Production and Recruitment to the Olfactory Bulb," *Society for Neuroscience* 25:1028 (1999) (abstract only).

During et al., "Towards Gene Therapy for the Central Nervous System," *Molecular Medicine Today* pp. 485-493 (1998).

Shihabuddin et al., "The Search for Neural Progenitor Cells: Prospects for the Therapy of Neurodegenerative Disease," *Molecular Medicine Today* 5:474-480 (1999).

Chalfie et al., "Green Fluorescent Protein as a Marker for Gene Expression," *Science* 263:802-805 (1994).

Luskin et al., "Neuronal Progenitor Cells Derived from the Anterior Subventricular Zone of the Neonatal Rat Forebrain Continue to Proliferate In vitro and Express Neuronal Phenotype," *Molecular and Cellular Neuroscience* 8:351-366 (1997).

Benraiss et al., "Adenoviral Transduction of the Ventricular Wall with a BDNF Expression Vector Induces Neuronal Recruitment from Endogenous Progenitor Cells in the Adult Forebrain," The Third Annual Meeting of the American Society of Gene Therapy, Colorado Convention Center, Denver, Colorado (May 1, 2000).

Kahn et al., "Thérapie Géniquedes Maladies Neurologiques," *C.R. Soc. Biol.* 190:9-11 (1996).

Benraiss et al., "Adenoviral Brain-Derived Neurotrophic Factor Induces Both Neostriatal and Olfactory Neuronal Recruitment From Endogenous Progenitor Cells in the Adult Forebrain," *The Journal of Neuroscience* 21(17):6718-6731 (2001).

Nunes et al., "Identification and Isolation of Multipotential Neural Progenitor Cells from the Subcortical White Matter of the Adult Human Brain," *Nature Medicine* 9(4):439-447 (2003).

Brüstle et al., "In vitro-Generated Neural Precursors Participate in Mammalian Brain Development," *Proc. Natl. Acad. Sci. USA* 94:14809-14814 (1997).

Azizi et al., "Engraftment and Migration of Human Bone Marrow Stromal Cells Implanted in the Brains of Albino Rats—Similarities to Astrocyte Grafts," *Proc. Natl. Acad. Sci. USA* 95:3908-3913 (1998).

"CytoTherapeutics' Researchers First to Directly Isolate Normal Human Neural Stem Cells," BW Health Wire News Release (Nov. 2, 1999), Reprint from Yahoo! Finance (Date Unknown).

Goldman et al., "Strategies Utilized by Migrating Neurons of the Postnatal Vertebrate Forebrain," *Trends in Neurosci.* 21(3):107-114 (1998).

Bachiller et al., "The Organizer Factors Chordin and Noggin are Required for Mouse Forebrain Development," *Nature* 403:658-661 (2000).

Gross et al., "Bone Morphogenetic Proteins Promote Astroglial Lineage Commitment by Mammalian Subventricular Zone Progenitor Cells," *Neuron* 17:595-606 (1996).

Li et al., "Neuronal Differentiation of Precursors in the Neocortical Ventricular Zone is Triggered by BMP," *J. Neurosci.* 18:8853-8862 (1998).

Li et al., "Noggin is a Negative Regulator of Neuronal Differentiation in Developing Neocortex," *Dev. Neurosci.* 22:68-73 (2000).

Mehler et al., "Developmental Changes in Progenitor Cell Responsiveness to Bone Morphogenetic Proteins Differentially Modulate Progressive CNS Lineage Fate," *Dev. Neurosci.* 22:74-85 (2000).

Mehler et al., "Cytokines Regulate the Cellular Phenotype of Developing Neural Lineage Species," *Int. J. Dev. Neurosci.* 13:213-240 (1995).

Menezes et al., "The Division of Neuronal Progenitor Cells During Migration in the Neonatal Mammalian Forebrain," *Mol. Cell. Neurosci.* 6:496-508 (1995).

Morshead et al., "Postmitotic Death is the Fate of Constitutively Proliferating Cells in the Subependymal Layer of the Adult Mouse Brain," *J. Neurosci.* 12:249-256 (1992).

Paine-Saunders et al., "Heparan Sulfate Proteoglycans Retain Noggin at the Cell Surface: A Potential Mechanism for Shaping Bone Morphogenetic Protein Gradients," *J. Biol. Chem.* 277:2089-2096 (2002).

Panchision et al., "Sequential Actions of BMP Receptors Control Neural Precursor Cell Production and Fate," *Genes & Dev.* 15:2094-2110 (2001).

Pencea et al., "Infusion of Brain-Derived Neurotrophic Factor into the Lateral Ventricle of the Adult Rat Leads to New Neurons in the Parenchyma of the Striatum, Septum, Thalamus and Hypothalamus," *J. Neurosci.* 21:6706-6717 (2001).

Valenzuela et al., "Identification of Mammalian Noggin and Its Expression in the Adult Nervous System," *J. Neurosci.* 15:6077-6084 (1995).

Zigova et al., "Intraventricular Administration of BDNF Increases the Number of Newly Generated Neurons in the Adult Olfactory Bulb," *Mol. Cell. Neurosci.* 11:234-245 (1998).

Chmielnicki et al., "Adenoviral Transduction of the Adult Rat Ventricular Zone to Overexpress Noggin Increases Local Neurogenesis and Neuronal Recruitment from Endogenous Progenitor Cells," *Molecular Therapy* 3(5):S319 (No. 898) (2001) (abstract).

Chmielnicki et al., "Adenoviral Infection of the Adult Rat Ventricular Zone to Overexpress Noggin and BDNF Increases Neuronal Recruitment from Endogenous Progenitor Cells," *Soc. Neuroscience* 27:939 (No. 361.4) (2001) (abstract).

Samdani et al., "Adenoviral BDNF Induces Neostriatal Neuronal Recruitment from Endogenous Progenitor Cells in Transgenic R6/2 Huntington Mice," *Molecular Therapy* 5(5):S300 (No. 919) (2002) (abstract).

Chmielnicki et al., "Adenoviral Co-Expression of Noggin and BDNF in the Adult Rat Ventricular Zone Synergistically Induces Neuronal Addition to the Neostriatum," *Molecular Therapy* 5(5):S438 (No. 1337) (2002) (abstract).

Chmielnicki et al., "Noggin Increases BDNF-Induced Striatal Neuronal Recruitment by Inhibiting Gliogenesis from Endogenous Progenitor Cells," *Soc. Neuroscience*, Abstract Viewer/Itinerary Planner, Program No. 113.12 (2002) (abstract).

Samdani et al., "Adenoviral BDNF Induces Endogenous Progenitor Cells to Regenerate New Striatal Neurons in R6/2 Mutant Huntington Mice," *Soc. Neuroscience*, Abstract Viewer/Itinerary Planner, Program No. 618.5 (2002) (abstract).

Emerich, D.F., "Neuroprotective Possibilities for Huntington's Disease," *Expert Opin. Biol. Ther.* 1:467-479 (2001).

Stewart et al., "Expression and Regulation of $\alpha 1\beta 1$ Integrin in Schwann Cells," *J. Neurobiology* 33(7):914-928 (1997).

Jackowski, "Neural Injury Repair: Hope for the Future as Barriers to Effective CNS Regeneration Become Clearer," *British J. Neurosurgery* 9:303-317 (1995).

Araujo et al., "Glial Cell Line-Derived Neurotrophic Factor Attenuates the Excitotoxin-Induced Behavioral and Neurochemical Deficits in a Rodent Model of Huntington's Disease," *Neuroscience* 81:1099-1110 (1997).

Anderson et al., "Ciliary Neurotrophic Factor Protects Striatal Output Neurons in an Animal Model of Huntington Disease," *PNAS* 93:7346-7351 (1996).

Frim et al., "Effects of Biologically Delivered NGF, BDNF, and bFGF on Striatal Excitotoxic Lesions," *NeuroReport* 4:367-370 (1993).

DeHamer et al., "Genesis of Olfactory Receptor Neurons in Vitro: Regulation of Progenitor Cell Divisions by Fibroblast Growth Factors," *Neuron* 13:1083-1097 (1994).

Deloulme et al., "Establishment of Pure Neuronal Cultures from Fetal Rat Spinal Cord and Proliferation of the Neuronal Precursor Cells in the Presence of Fibroblast Growth Factor," *J. Neurosci. Res.* 29:499-509 (1991).

DiCicco-Bloom et al., "Insulin Growth Factors Regulate the Mitotic Cycle in Cultured Rat Sympathetic Neuroblasts," *Proc. Natl. Acad. Sci. USA* 85:4066-4070 (1988).

Drago et al., Fibroblast Growth Factor-Mediated Proliferation of Central Nervous System Precursors Depends on Endogenous Production of Insulin-Like Growth Factor I, *Proc. Natl. Acad. Sci. USA* 88:2199-2203 (1991).

Gensburger et al., "Brain Basic Fibroblast Growth Factor Stimulates the Proliferation of Rat Neuronal Precursor Cells In Vitro," *FEBS Lett.* 217:1-5 (1987).

Kilpatrick et al., "Cloned Multipotential Precursors from the Mouse Cerebrum Require FGF-2, Whereas Glial Restricted Precursors are Stimulated with Either FGF-2 or EGF," *J. Neurosci.* 15:3653-3661 (1995).

Kitchens et al., "FGF and EGF are Mitogens for Immortalized Neural Progenitors," *J. Neurobiol.* 25:797-807 (1994).

Lendahl et al., "CNS Stem Cells Express a New Class of Intermediate Filament Protein," *Cell* 60:585-595 (1990).

Lillien et al., "Type-2 Astrocyte Development in Rat Brain Cultures is Initiated by a CNTF-Like Protein Produced by Type-1 Astrocytes," *Neuron* 1:485-494 (1988).

McKinnon et al., "Distinct Effects of bFGF and PDGF on Oligodendrocyte Progenitor Cells," *Glia* 7:245-254 (1993).

Murphy et al., "Fibroblast Growth Factor Stimulates the Proliferation and Differentiation of Neural Precursor Cells In Vitro," *J. Neurosci. Res.* 25:463-475 (1990).

Murphy et al., "Generation of Sensory Neurons is Stimulated by Leukemia Inhibitory Factor," *Proc. Natl. Acad. Sci. USA* 88:3498-3501 (1991).

Murphy et al., "FGF2 Regulates Proliferation of Neural Crest Cells, with Subsequent Neuronal Differentiation Regulated by LIF or Related Factors," *Development* 120:3519-3528 (1994).

Pincus et al., "Vasoactive Intestinal Peptide Regulates Mitosis, Differentiation and Survival of Cultured Sympathetic Neuroblasts," *Nature* 343:564-567 (1990).

Qian et al., "FGF2 Concentration Regulates the Generation of Neurons and Glia from Multipotent Cortical Stem Cells," *Neuron* 18:81-93 (1997).

Raff et al., "A Glial Progenitor Cell that Develops In Vitro into an Astrocyte or an Oligodendrocyte Depending on Culture Medium," *Nature* 303:390-396 (1983).

Raff et al., "Platelet-Derived Growth Factor from Astrocytes Drives the Clock that Times Oligodendrocyte Development in Culture," *Nature* 333:562-565 (1988).

Ray et al., "Proliferation, Differentiation, and Long-Term Culture of Primary Hippocampal Neurons," *Proc. Natl. Acad. Sci. USA* 90:3602-3606 (1993).

Ray et al., "Spinal Cord Neuroblasts Proliferate in Response to Basic Fibroblast Growth Factor," *J. Neurosci.* 14:3548-3564 (1994).

Reynolds et al., "A Multipotent EGF-Responsive Striatal Embryonic Progenitor Cell Produces Neurons and Astrocytes," *J. Neurosci.* 12:4565-4574 (1992).

Reynolds et al., "Generation of Neurons and Astrocytes from Isolated Cells of the Adult Mammalian Central Nervous System," *Science* 255:1707-1710 (1992).

Santa-Olalla et al., "Epidermal Growth Factor (EGF), Transforming Growth Factor-60 (TFG-α), and Basic Fibroblast Growth Factor (bFGF) Differentially Influence Neural Precursor Cells of Mouse Embryonic Mesencephalon," *J. Neurosci. Res.* 42:172-183 (1995).

Shah et al., "Glial Growth Factor Restricts Mammalian Neural Crest Stem Cells to a Glial Fate," *Cell* 77:349-360 (1994).

Temple et al., "Differentiation of a Bipotential Glial Progenitor Cell in a Single Cell Microculture," *Nature* 313:223-225 (1985).

Wolswijk et al., "Cooperation Between PDGF and FGF Converts Slowly Dividing O-2A$^{Adult}$ Progenitor Cells to Rapidly Dividing Cells with Characteristics of O-2A$^{Perinatal}$ Progenitor Cells," *J. Cell. Biol.* 118:889-900 (1992).

Grinspan et al., "Platelet-Derived Growth Factor is a Survival Factor for PSA-NCAM+ Oligodendrocyte Pre-Progenitor Cells," *J. Neurosci. Res.* 41:540-551 (1995).

Pincus et al., "In vitro Neurogenesis by Adult Human Epileptic Temporal Neocortex," *Clinical Neurosurgery* 44:17-25 (1997).

Friedmann, "Overcoming the Obstacles to Gene Therapy," *Scientific American* 276(6):96-101 (1997).

Orkin et al., "Report and Recommendations of the Panel to Assess the NIH Investment in Research on Gene Therapy," available at http://www.nih.gov/news/panelrep.html (Dec. 7, 1995).

Verma et al., "Gene Therapy: Promises, Problems and Prospects," *Nature* 389(6648):239-242 (1997).

\* cited by examiner

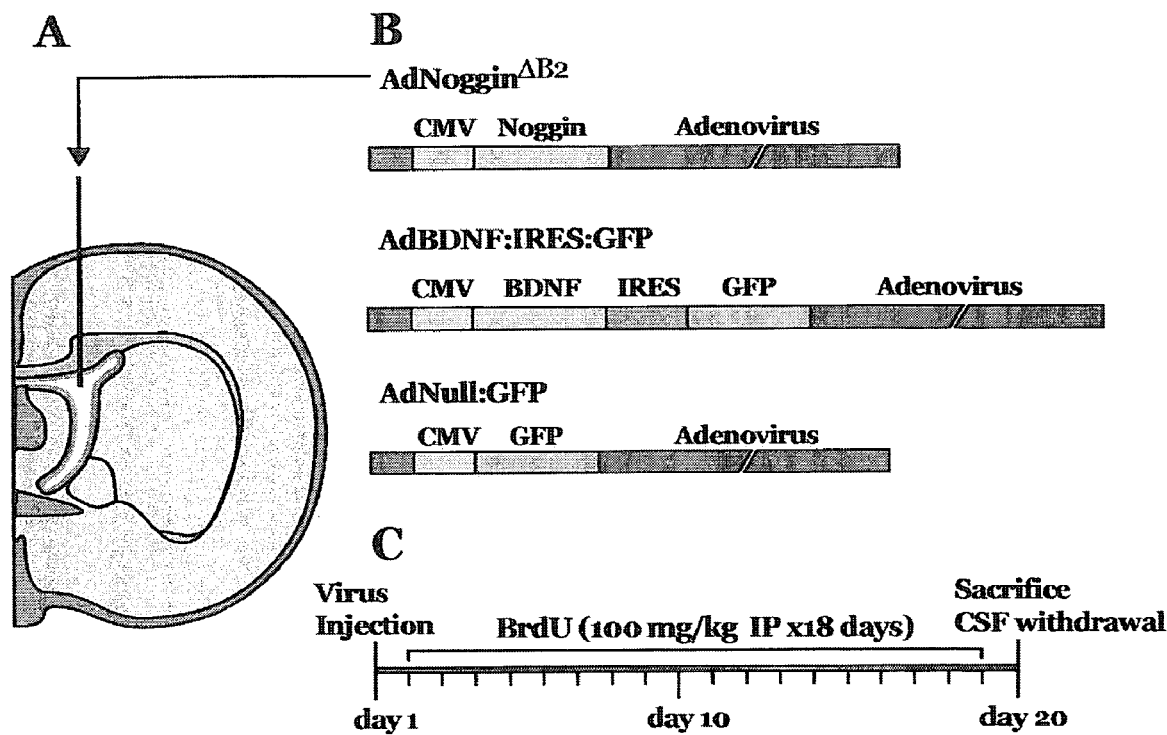
Figures 1A-C

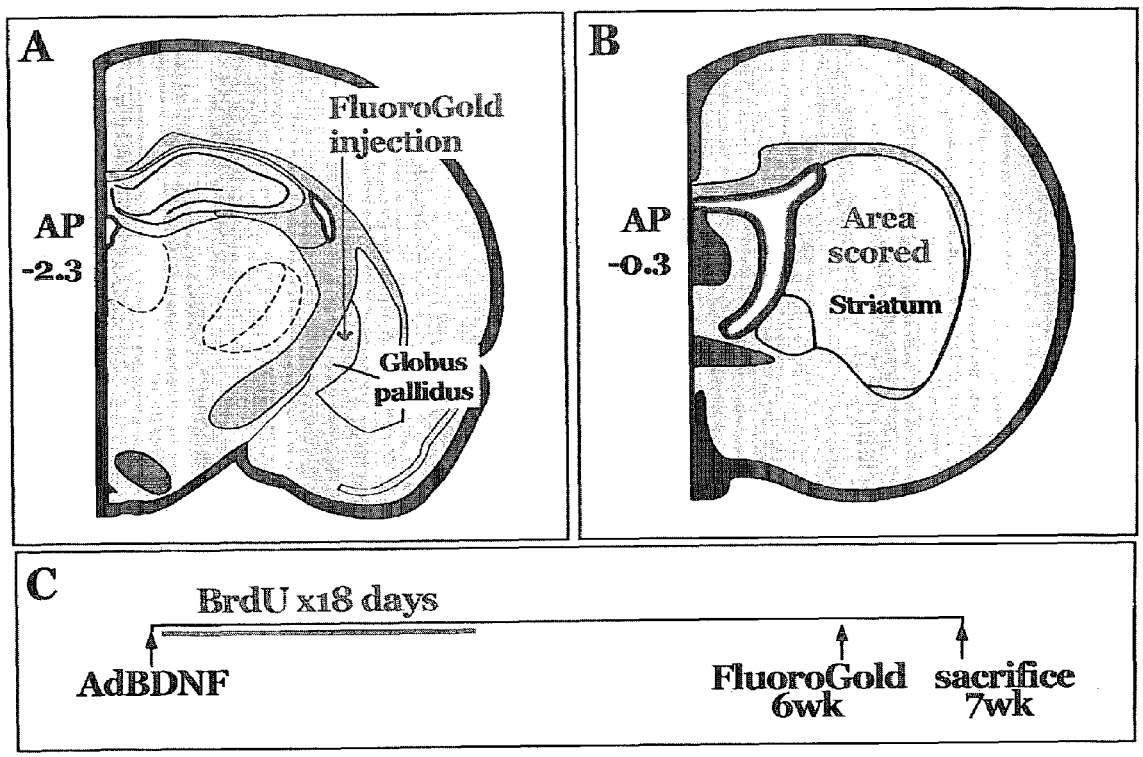
Figures 2A-C

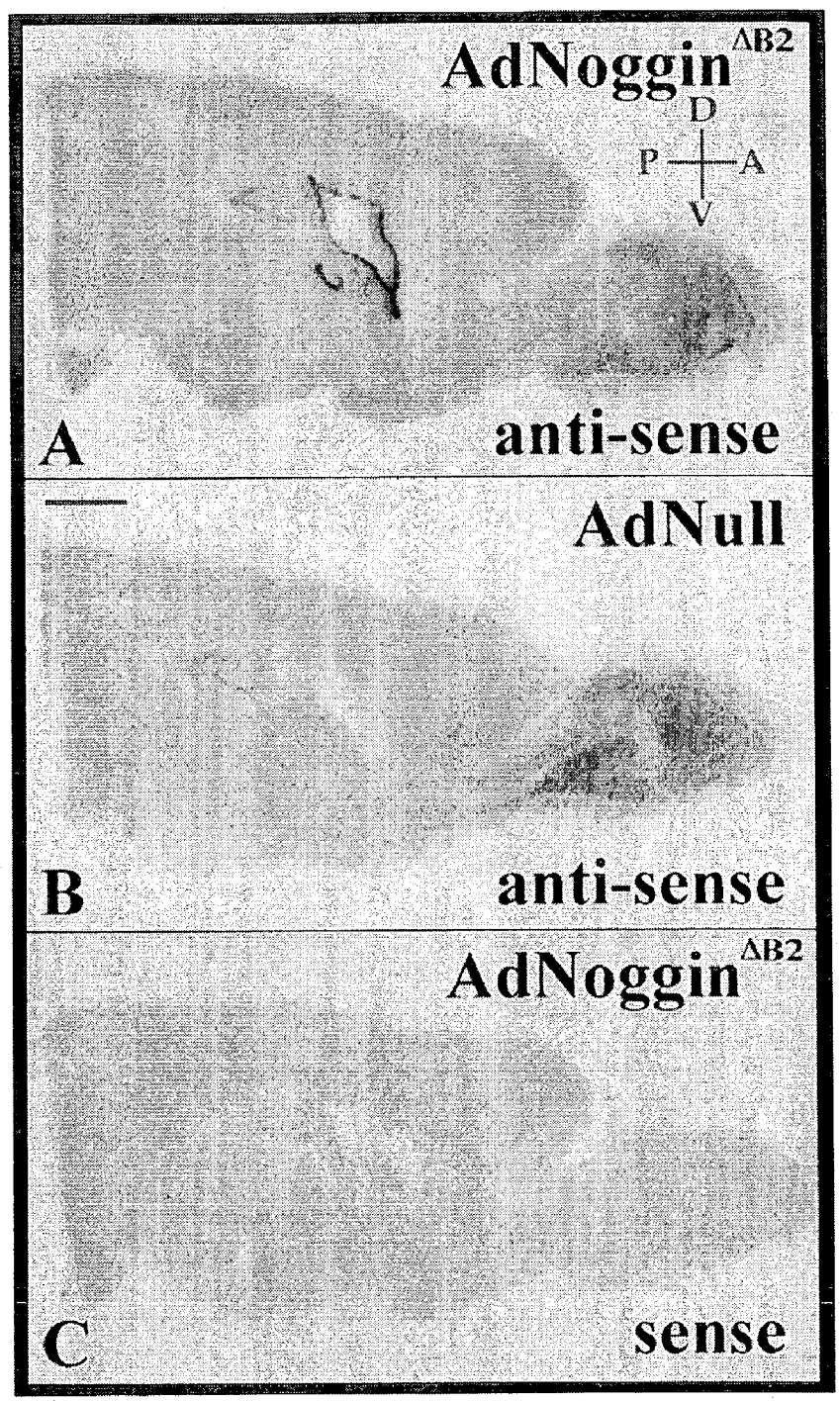
Figures 3A-C

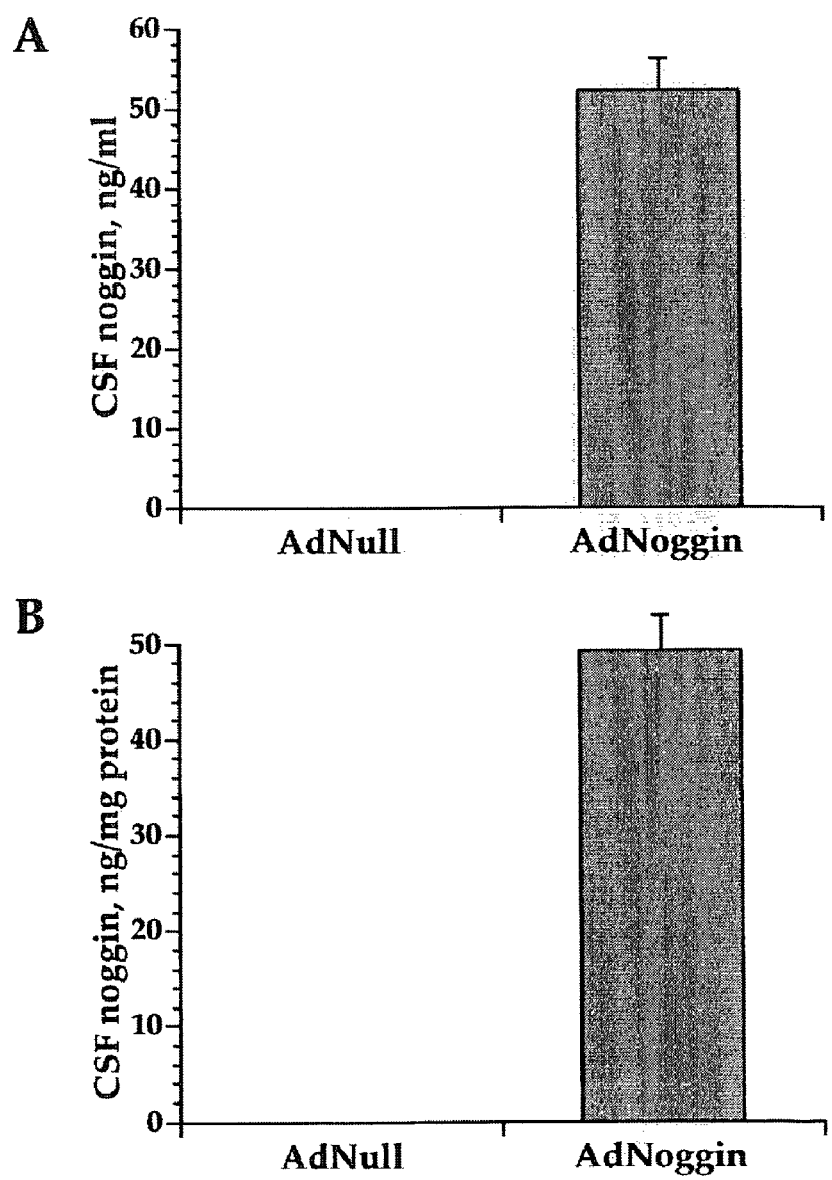
Figures 4A-B

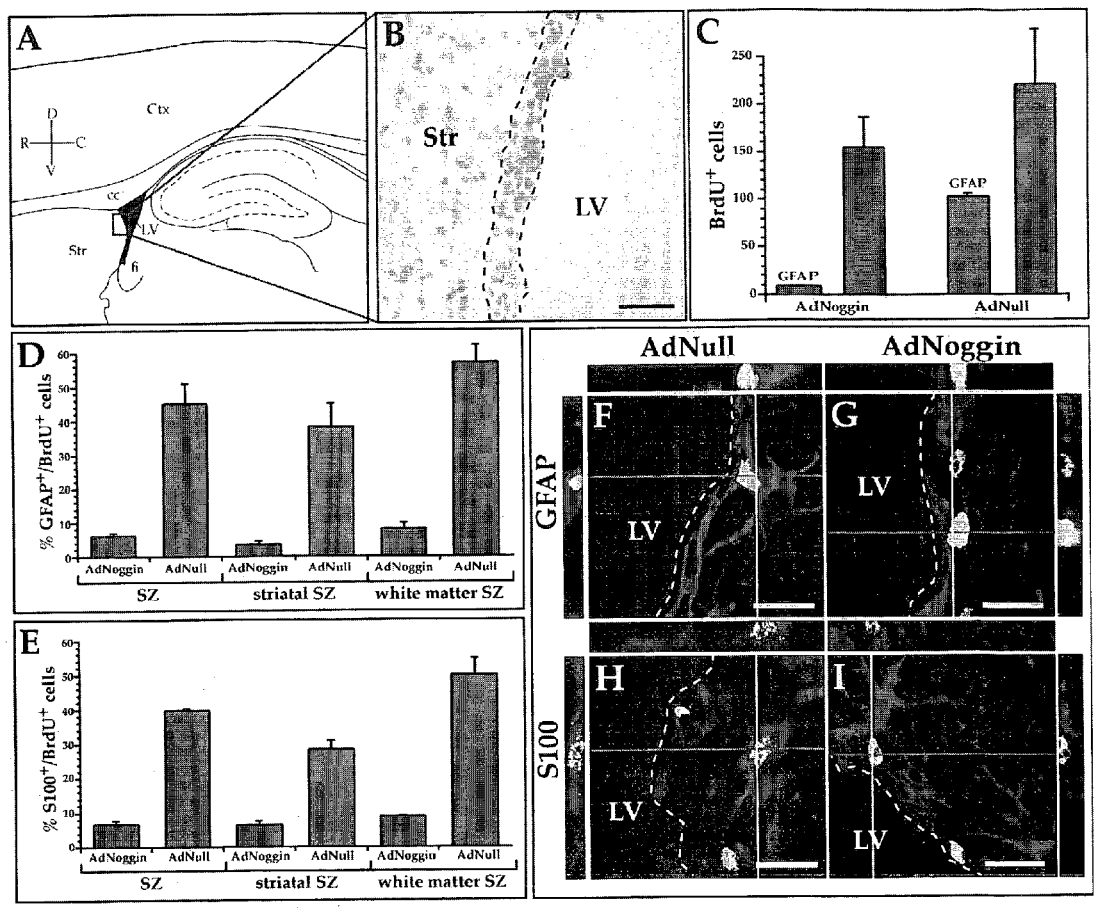
Figures 5A-I

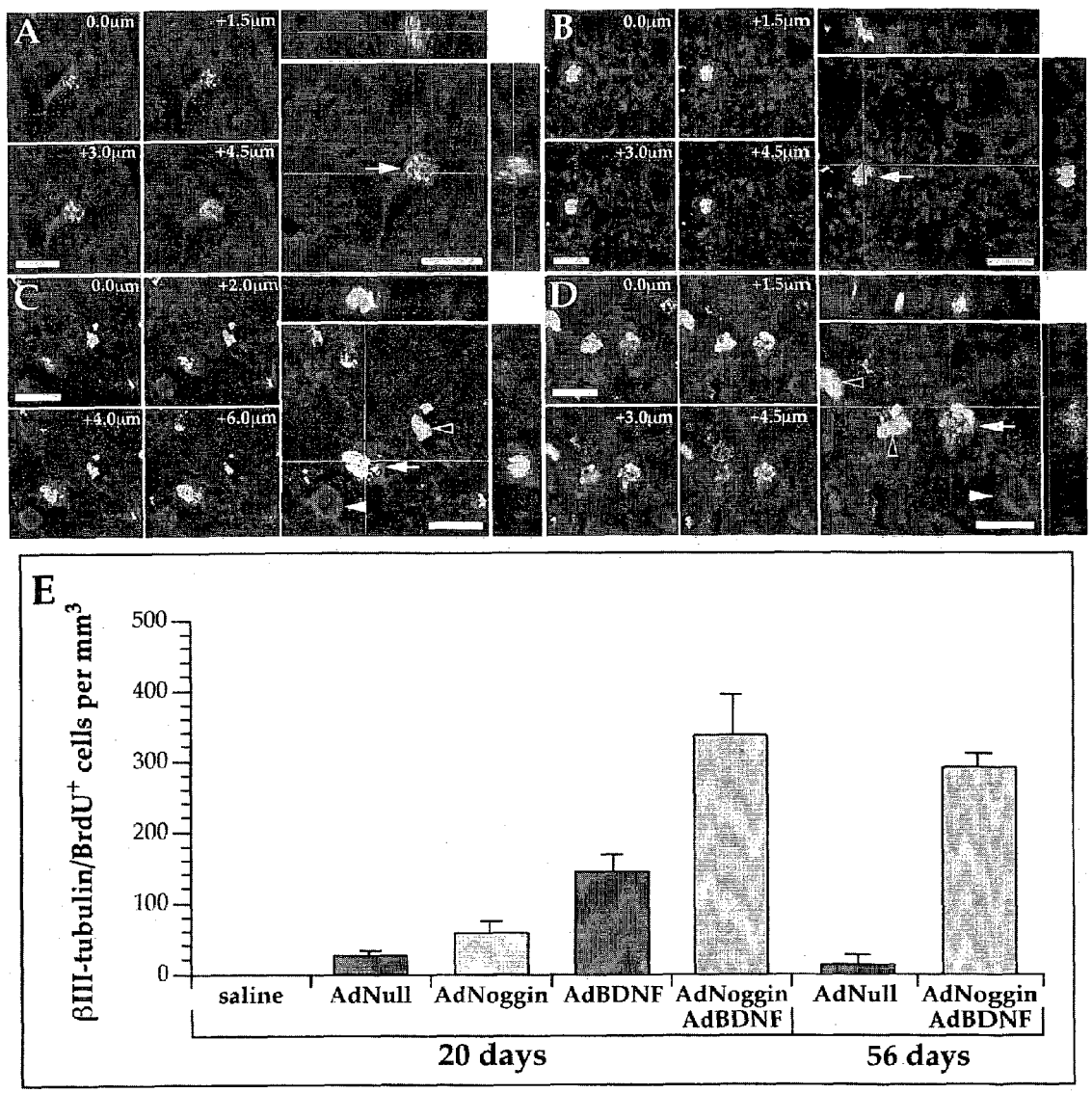
Figures 6A-E

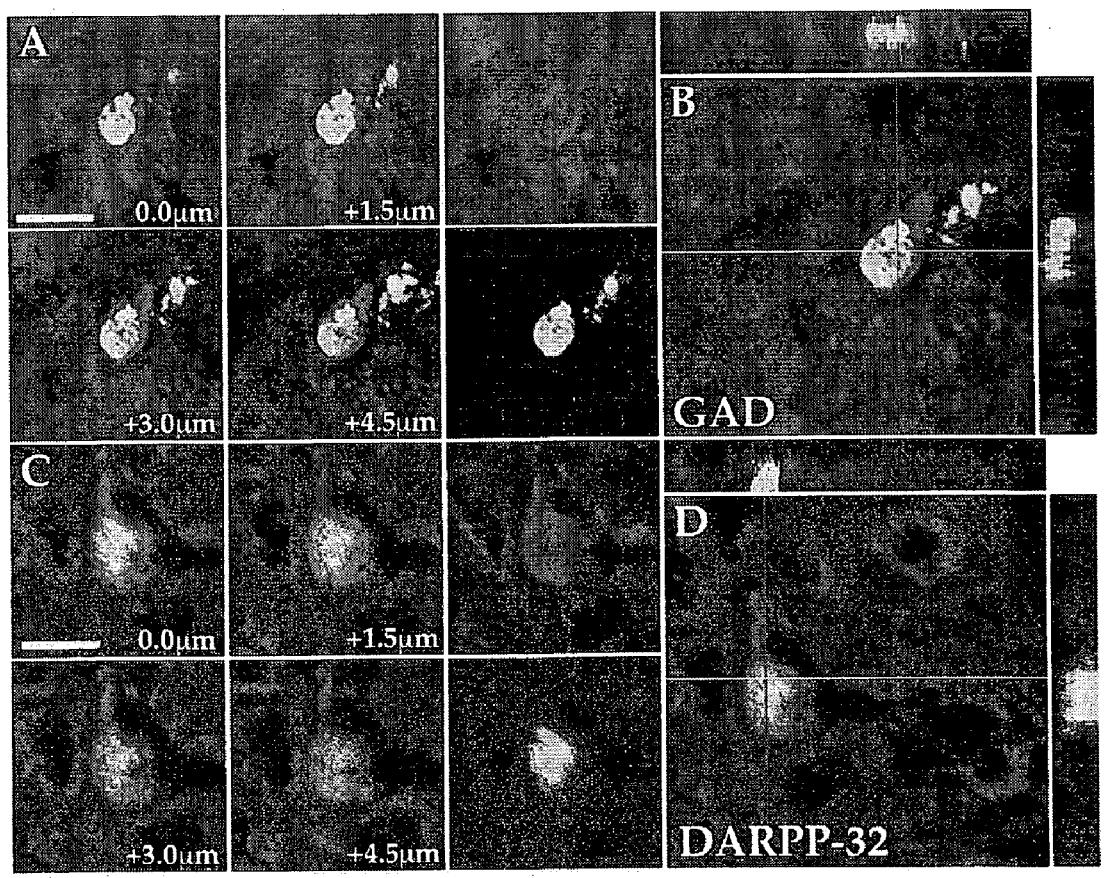
Figures 7A-D

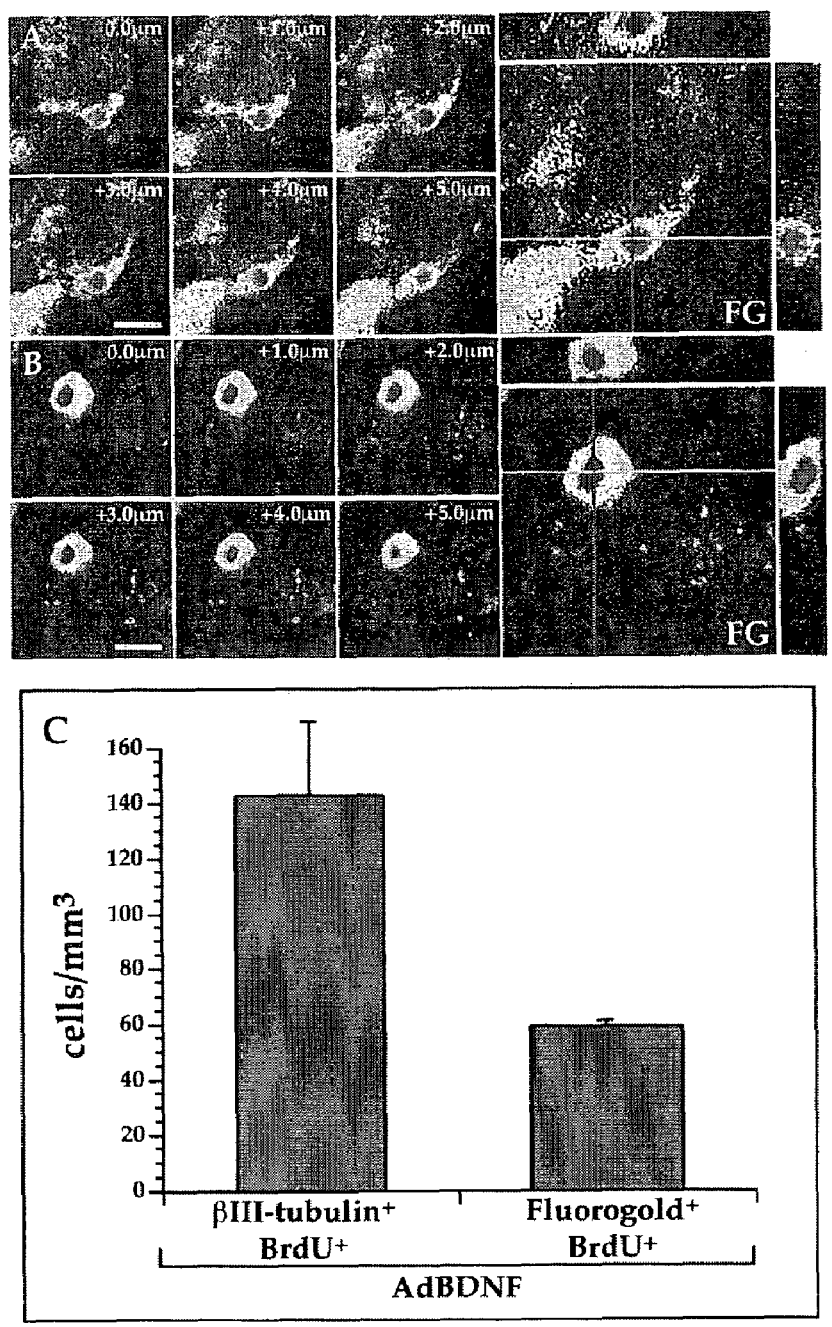
Figures 8A-C

ENHANCING NEUROTROPHIN-INDUCED NEUROGENESIS BY ENDOGENOUS NEURAL PROGENITOR CELLS BY CONCURRENT OVEREXPRESSION OF BRAIN DERIVED NEUROTROPHIC FACTOR AND AN INHIBITOR OF A PRO-GLIOGENIC BONE MORPHOGENETIC PROTEIN

This application claims benefit of U.S. Provisional Patent Application Serial No. 60/358,005, filed Feb. 15, 2002.

The subject matter of this application was made with support from the United States National Institutes of Health Grant Nos. NINDS R01NS33106. The United States Government may have certain rights.

FIELD OF THE INVENTION

The present invention relates to a method of inducing neuronal production in a subject, a method of recruiting neurons to a subject's brain, a method of treating a neurodegenerative condition, a method of suppressing astrocyte generation and inducing neuronal production in a subject, a method of treating a neurologic condition, and a method of introducing a therapeutic protein into a subject's brain and spinal cord.

BACKGROUND OF THE INVENTION

Neural progenitor cells persist throughout the adult forebrain ventricular zone (VZ), and have been found in species ranging from canaries to humans (Alvarez-Buylla et al., "Neuronal Stem Cells in the Brain of Adult Vertebrates," *Stem Cells* 13:263-72, (1995); Goldman, S. et al., "Neuronal Precursor Cells of the Adult Rat Ventricular Zone Persist into Senescence, with No Change in Spatial Extent or BDNF Response," *J. Neurobiology* 32:554-566 (1997); Goldman, S. et al., "Neural Precursors and Neuronal Production in the Adult Mammalian Forebrain," *Ann. N.Y. Acad. Sci.* 835:30-55 (1997); Goldman, S. A. et al., "Strategies Utilized by Migrating Neurons of the Postnatal Vertebrate Forebrain," *Trends in Neurosciences* 21:107-114 (1998)). To the extent that neurogenesis and oligoneogenesis by these endogenous progenitors may be induced or supported exogenously, these cells may provide a cellular substrate for repair in the adult central nervous system (CNS). In culture, adult-derived progenitors have been found to respond to mitogens, in particular epidermal growth factor (EGF) and fibroblast growth factor 2 (FGF2), with increased division and neuronal mitogenesis (Palmer, T. D. et al, "FGF-2-Responsive Neuronal Progenitors Reside in Proliferative and Quiescent Regions of the Adult Rodent Brain," *Mol. Cell Neurosci.* 6:474-86 (1995); Reynolds, B. A. et al, "Generation of Neurons and Astrocytes from Isolated Cells of the Adult Mammalian Central Nervous System," *Science* 255:1707-10 (1992); Richards, L. J. et al, "De Novo Generation of Neuronal Cells from the Adult Mouse Brain," *Proc. Nat'l. Acad. Sci. USA* 89:8591-5 (1992); Vescovi, A. L. et al, "bFGF Regulates the Proliferative Fate of Unipotent (neuronal) and Bipotent (neuronal/astroglial) EGF-generated CNS Progenitor Cells," *Neuron* 11:951-66, (1993)). Furthermore, neurons generated from them respond to brain-derived neurotrophic factor (BDNF) with enhanced migration, maturation, and survival in vitro (Goldman, S. et al., "Neuronal Precursor Cells of the Adult Rat Ventricular Zone Persist into Senescence, with No Change in Spatial Extent or BDNF Response," *J. Neurobiology* 32:554-566 (1997); Goldman, S. et al., "Neural Precursors and Neuronal Production in the Adult Mammalian Forebrain," *Ann. N.Y. Acad. Sci.* 835:30-55 (1997); Kirschenbaum, B. et al, "Brain-derived Neurotrophic Factor Promotes the Survival of Neurons Arising from the Adult Rat Forebrain Subependymal Zone," *Proc. Nat'l. Acad. Sci. USA* 92:210-4 (1995)). Similarly, infusions of EGF and FGF2 into the adult ventricular system stimulate mitotic gliogenesis and neurogenesis, respectively (Craig, C. G. et al., "In Vivo Growth Factor Expansion of Endogenous Subependymal Neural Precursor Cell Populations in the Adult Mouse Brain," *J. Neuroscience* 16:2649-58 (1996); Kuhn, H. G. et al, "Epidermal Growth Factor and Fibroblast Growth Factor-2 Have Different Effects on Neural Progenitors in the Adult Rat Brain," *J. Neuroscience* 17:5820-5829 (1997)), while intraventricular infusions of BDNF can enhance neuronal migration to the olfactory bulb, rostral migratory stream, and adjacent forebrain (Pencea, V. et al, "Infusion of BDNF into the Lateral Ventricle of the Adult Rat Leads to an Increase in the Number of Newly Generated Cells in the Fore-, Mid- and Hindbrain Parenchyma," *Soc. Neurosci. Abstr.* 25:2045 (1999); Zigova, T. et al., "Intraventricular Administration of BDNF Increases the Number of Newly Generated Neurons in the Adult Olfactory Bulb," *Molec. Cellular Neurosci.* 11:234-245 (1998)). Although intriguing, these studies have been limited by the need for chronic intraventricular catheterization, with its dependence upon protein availability and stability, the uncertain tissue bioavailability of intraventricularly administered proteins, and the risks of infection and catheter loss inherent in chronic ventriculostomy.

The striatum is the major target of the progressive neurodegeneration that occurs in Huntington's Disease, in which the major neuron loss is that of the striatal GABA-producing neurons. Other degenerative diseases, such as amyotrophic lateral sclerosis (ALS; also known as Lou Gehrig's Disease), and progressive muscular atrophy, result at least in part from a decay of motor neurons which are located in the ventral horn of the spinal cord.

While there are some therapies available to treat the symptoms and decrease the severity of such diseases (e.g., L-dopa to treat Parkinson's Disease), there currently exists no effective treatment to prevent or reduce the degeneration of most of the above-mentioned classes of affected neurons, or to promote their repair. Several naturally-occurring proteins have been identified based on their trophic activity on various neurons. These molecules are termed "neurotrophic factors". Neurotrophic factors are endogenous, soluble proteins that can stimulate or regulate the production, survival, growth, and/or morphological plasticity of neurons. (See Fallon and Laughlin, *Neurotrophic Factors,* Academic Press, San Diego, Calif. (1993)).

The known neurotrophic factors belong to several different protein superfamilies of polypeptide growth factors based on their amino acid sequence homology and/or their three-dimensional structure (MacDonald et al., "A Structural Superfamily Of Growth Factors Containing A Cystine Knot Motif," *Cell* 73:421-424 (1993)). One family of neurotrophic factors is the neurotrophin family. This family currently consists of nerve growth factor (NGF), brain derived neurotrophic factor (BDNF), neurotrophin-3 (NT-3), neurotrophin-4 (NT-4), and neurotrophin-6 (NT-6).

On the basis of current studies, and of their limitations in practice, it will be appreciated that a need exists for an efficient means of delivering neurotrophic differentiation agents to the adult ventricular zone, the site of residual progenitor cells in the adult brain. Furthermore, in view of the fact that many nervous system disorders and diseases have no known cure, there is a need in the art for new methods of inducing neuronal production in the adult brain, especially for treating Huntington's Disease and other degenerative neurological conditions, as well as stroke and traumatic brain injury.

The present invention is directed to overcoming these and other deficiencies in the art.

SUMMARY OF THE INVENTION

The present invention relates to a method of inducing neuronal production in a subject. This includes providing a neurotrophic factor and providing an inhibitor of pro-gliogenic bone morphogenetic proteins (BMP). The neurotrophic factor and the inhibitor are administered into the subject's lateral ventricles or ventricular zone wall under conditions effective to induce neuronal production in the brain and spinal cord of the subject.

Another aspect of the present invention relates to a method of recruiting neurons to a subject's brain. This embodiment of the present invention comprises providing a neurotrophic factor and providing an inhibitor of pro-gliogenic bone morphogenetic proteins. The neurotrophic factor and the inhibitor are then administered into the subject's lateral ventricles or ventricular wall under conditions effective to recruit neurons to the brain of the subject. This method is particular useful for recruiting new neurons to a damaged or diseased region of a subject's brain.

A further aspect of the present invention relates to a method of treating a neurodegenerative condition by providing a neurotrophic factor and an inhibitor of pro-gliogenic bone morphogenetic proteins. The neurotrophic factor and the inhibitor are administered into the subject's lateral ventricles or ventricular wall under conditions effective to treat a neurodegenerative condition.

Another embodiment of the present invention relates to a method of suppressing astrocyte generation and inducing neuronal production in a subject. In this method, an inhibitor of pro-gliogenic bone morphogenctic proteins is provided and the inhibitor is administered into the subject's lateral ventricles or ventricular wall under conditions effective to suppress astrocyte generation and induce neuronal production in the brain and spinal cord of the subject.

A further aspect of the present invention pertains to a method of treating a neurologic condition in a subject. This method includes providing an inhibitor of pro-gliogenic bone morphogenetic proteins and administering the inhibitor to the subject's lateral ventricles, ventricular wall, or site of injury under conditions effective to treat a neurologic condition.

Another aspect of the present invention relates to a method of suppressing glial scar formation in a subject. This method involves providing an inhibitor of progliogenic bone morphogenetic proteins. The inhibitor of progliogenic bone morphogenic proteins is administered to the subject's ventricles, ventricular wall, or sites of injury at risk for glial scar formation under conditions effective to suppress glial scar formation in the subject.

The present invention also relates to a method of introducing a therapeutic protein into a subject's brain and spinal cord. In this method, a nucleic acid molecule encoding the therapeutic protein introduced into the subject's ependyma. The protein from the nucleic acid molecule is then expressed within the subject's ependyma, and the expressed protein is permitted to migrate within the subject's brain and spinal cord.

BDNF promotes the neuronal differentiation and survival of newly generated SZ daughter cells (Ahmed et al., *J Neurosci* 15:5765-78 (1995) and Kirschenbaum et al., *Proc Natl Acad Sci U S A* 92:210-4 (1995), which are hereby incorporated by reference in their entirety). In the absence of BDNF, these same daughter cells might otherwise generate glia, or, alternatively, may undergo apoptotic death (Morshead et al., *The Journal of Neuroscience* 12:249-256 (1992), which is hereby incorporated by reference in its entirety). Together, these observations raised the possibility that SZ progenitors might be driven to neuronal phenotype not only by promoting neuronal differentiation, but also by suppressing glial differentiation. This possibility was testable, in that a number of humoral glial differentiation agents and their inhibitors have been identified. In particular, the bone morphogenetic proteins drive neural progenitors to glial fate, in the adult and late fetal rodent brain (Gross et al., *Neuron* 17:595-606 (1996) and Lim et al., *Neuron* 28:713-726 (2000), which are hereby incorporated by reference in their entirety). In the adult forebrain SZ, both the BMPs and their receptors are abundant (Gross et al., *Neuron* 17:595-606 (1996) and Mehler et al., *Int J Dev Neurosci* 13:213-40 (1995), which are hereby incorporated by reference in their entirety), in accord with the gliogenic bias of most of the adult subependyma. Therefore, applicants reasoned that overexpression of noggin, a soluble BMP inhibitor (Zimmerman et al., *Cell* 86:599-606 (1996), which is hereby incorporated by reference in its entirety), might suppress astroglial differentiation of SZ cells, and thereby promote their neuronal differentiation. Indeed, noggin expression has been shown to persist in some regions of ongoing neurogenesis in the adult rodent brain (Lim et al., *Neuron* 28:713-726 (2000), which is hereby incorporated by reference in its entirety). Furthermore, applicants postulated that by suppressing glial differentiation, noggin might make more SZ daughter cells responsive to neuronal instruction by BDNF, thereby providing a concurrently permissive and instructive environment for neurogenesis.

To this end, noggin was overexpressed in the ventricular wall of adult rats, and it was found that noggin substantially suppressed gliogenesis throughout the lateral ventricular subependyma. Both glial fibrillary acidic protein (GFAP) and S-100β protein-defined astrocytes, defined as newly generated by their incorporation of bromodeoxyuridine (BrdU), or substantially suppressed by adenoviral noggin (AdNoggin) suppression.

Furthermore, co-injection of adenoviral BDNF (AdBDNF) and AdNoggin resulted in a dramatic increase in neuronal addition to the striatum, a typically non-neurogenic region, and did so to a much greater extent than did AdBDNF injection alone (Benraiss et al., *J Neurosci* 21:6718-31 (2001), which is hereby incorporated by reference in its entirety). The newly generated striatal neurons expressed the antigenic phenotype of medium spiny neurons of the caudate-putamen. Over the 2 month period following their genesis, Fluorogold backfills revealed that these cells extended fibers to their usual target, the globus pallidus. These new pallidal projection neurons survived and integrated, indicating that induced neurogenesis from resident progenitor cells might achieve the growth or regrowth of multinuclear circuits in the adult forebrain.

BRIEF DESCRIPTION OF THE DRAWINGS

FIG S. 1A-C shows a strategy for inducing and tracking adult neuronal recruitment. FIG. 1A is a schematic of coronal section showing site of injection of adenovirus into the lateral ventricle. In FIG. 1B, ΔE1 adenoviral type 5 constructs were constructed to express noggin$^{\Delta B2}$, hGFP (as a control vector) or BDNF:IRES:GFP, all under the control of the constitutive promoter CMV. FIG. 1C is a schematic of the experimental protocol: Adenovirus was injected on day 1, followed by i.p. injections of 100 mg/kg bromodeoxyuridine (BrdU) for the next 18 days. On day 20, the rats were sacrificed, their cerebrospinal fluid (CSF) withdrawn for noggin enzyme-linked immunosorbent assay (ELISA), and the brains processed for BrdU histochemistry and phenotype-specific immunolabeling.

FIGS. 2A-C shows the strategy for determining if AdBDNF-induced striatal cells are projection neurons. FIGS. 2A-B are schematic drawings of coronal sections showing site of injection of Fluorogold into the globus pallidus (FIG. 2A) and a region of striatum scored for the incidence of BrdU$^+$/Fluorogold$^+$ cells (FIG. 2B). Anteroposterior (AP) coordinates are as noted; the distance between pallidal injection site and striatal region of neuronal recruitment $\geq$2 mm. FIG. 2C is a schematic of the experimental protocol: Adenovirus was injected into the lateral ventricle on day 1, followed by i.p. injections of 100 mg/kg BrdU for the next 18 days. Six weeks after adenoviral injection, Fluorogold was injected into the globus pallidus. A week later, the rats were sacrificed, and the brains were processed for BrdU histochemistry.

FIGS. 3A-C show the intraventricular AdNoggin$^{\Delta B2}$ targets viral transgene overexpression to the ventricular wall. In FIGS. 3A-C, sagittal sections of AdNoggin$^{\Delta B2}$ (FIGS. 3A and C) or AdNull injected rat brains (FIG. 3B) were treated with anti-sense (FIGS. 3A-B) or sense (FIG. 3C) probes for mouse noggin. Expression of the viral ansgene is limited to the wall of the lateral ventricle. D, dorsal; V, ventral; A, anterior; P, posterior. Scale bar, 2 mm.

FIGS. 4A-B show that intraventricular AdNoggin$^{\Delta B2}$ increased noggin protein levels in the CSF. AdNoggin$^{\Delta B2}$ injected animals showed sustained expression of high levels of noggin protein in the CSF, measured at day 20, when compared with AdNull-injected controls (n=3 rats/group). FIG. 4A presents the results in ng/ml, while FIG. 4B is in ng/mg protein.

FIGS. 5A-I show that AdNoggin suppresses glial production by the adult VZ. FIG. 5A is a schematic of sagittal rat brain section, indicating the subependymal zone (SZ) scored for the incidence of BrdU$^+$/GFAP$^+$-S100$\beta^+$ cells. The area in the box is shown in more detail in FIG. 5B as a cresyl violet-stained section, with the SZ bordered by the dotted lines. Scale=64 μm. FIG. 5C shows that despite a stable incidence of total ventricular zone BrdU labeling between AdNoggin- and AdNull-injected animals, AdNoggin-injected rats exhibited substantial lower frequencies of BrdU$^+$/GFAP$^+$ subependymal astrocytes. In the graphs of FIGS. 5D-E, the subependyma—which has a roughly triangular profile in sagittal section—was divided into the striatal and callosal/fimbrial white matter segments, each of which was scored independently for (FIG. 5D) GFAP$^+$/BrdU$^+$ and (FIG. 5E) S100$\beta^+$/BrdU$^+$ cells. In all regions of the lateral ventricular lining, AdNoggin-injected rats exhibited substantial lower frequencies of BrdU$^+$/GFAP$^+$ subependymal astrocytes. FIGS. 5F-I show orthogonal views of subependymal BrdU$^+$, as viewed in the xz and yz planes, verified by co-labeling with GFAP (FIGS. 5F-G) and S100$\beta$ (FIGS. 5H-I). Fewer BrdU$^+$ cells co-labeled with the astrocytic markers in AdNoggin-injected rats (FIGS. 5G and I) than in AdNull-injected animals (FIGS. 5F and H). Scale bars, 16 μm. D, dorsal; V, ventral; R, rostral; C, caudal; Ctx, cortex; cc, corpus callosum; LV, lateral ventricle; fi, fimbria; Str, striatum; SZ, subependymal zone.

FIGS. 6A-E show that AdNoggin$^{\Delta B2}$ significantly increased AdBDNF-induced neuronal addition to the striatum. FIGS. 6A-D show confocal images of newly generated neurons (arrows), double-immunostained for β-III tubulin$^+$ and BrdU$^+$, in the striata of rats injected either 20 (FIGS. 6A-B) or 56 (FIGS. 6C-D) days previously with both AdBDNF and AdNoggin. Left, serially acquired confocal images, stacked and shown as an orthogonal view, right. Filled arrowheads indicate β-III tubulin$^+$ cells that did not incorporate BrdU, while empty arrowheads indicate BrdU$^+$ cells that are not neuronal. Scale bars=16 μm. FIG. 6E shows the mean density of β-III tubulin$^+$/BrdU$^+$ cells in the neostriata of saline-, AdNull-, AdNoggin$^{\Delta B2}$-, AdBDNF-, and AdNoggin$^{\Delta B2}$/AdBDNF-injected rats, as compared between animals sacrificed on day 20 (left) and day 56 (right).

FIGS. 7A-D show that AdNoggin/AdBDNF-induced striatal neurons express markers characteristic of medium spiny neurons. These figures are confocal images of GAD67$^+$/BrdU$^+$ or DARPP-32$^+$/BrdU$^+$ double-immunolabeled cells in the striata of AdBDNF/AdNoggin-injected rats (20 day survival). Left, four serially displayed confocal optical sections, shown 1.5 μm apart, accompanied by color split images. Right, reconstructed orthogonal images, as viewed from the side in both the xz and yz planes. Scale bars, 16 μm.

FIGS. 8A-C show that newly generated striatal neurons project to the globus pallidus. FIGS. 8A-B are confocal images of Fluorogold$^+$/BrdU$^+$ double-immunolabeled cells in the striata of AdBDNF-injected rats (7 week survival). These rats received Fluorogold injections to the globus pallidus 6 weeks after intraventricular AdBDNF injection, and were sacrificed one week later. Left, six serially displayed confocal optical sections, shown 1.0 μm apart. Right, reconstructed side views, as viewed in both the xz and yz planes. Scale=16 μm. FIG. 8C shows the mean density of BrdU$^+$/β-III tubulin$^+$ and BrdU$^+$/Fluorogold$^+$ cells in the neostriata of AdBDNF-injected animals.

DETAILED DESCRIPTION OF THE INVENTION

The present invention relates to a method of inducing neuronal production in a subject. This includes providing a neurotrophic factor and providing an inhibitor of pro-gliogenic bone morphogenetic proteins. The neurotrophic factor and the inhibitor are administered into the subject's lateral ventricles or ventricular zone wall under conditions effective to induce neuronal production in the brain and spinal cord of the subject.

Neuronal production as used herein refers to the generation of new neurons. One type of nucleic acid suitable for the present invention are nucleic acids which encode growth factor products, in particular neurotrophic growth factors. Such nucleic acids include, but are not limited to, the nucleic acid encoding BDNF, the neurotrophins NT-3 (Regeneron, Tarrytown, N.Y.) and NT-4/NT-5, insulin-like growth factor, nerve growth factor (NGF), the recently identified neurotrophic family of factors designated "NNT" (see U.S. Pat. No. 6,143,874 to Chang, which is hereby incorporated by reference in its entirety), ciliary neurotrophic factor (CNTF), and the interleukins. Besides being administered as a nucleic acid construct encoding a neurotrophic factor, the neurotrophic factor can be administered in the form of a protein or polypeptide.

In the brain, a protein known as bone morphogenic protein drives progenitor cells to differentiate into glial cells. Noggin is a developmental molecule which suppresses bone morphogenic protein in the brain. Without the influence of bone morphogenic protein, progenitor cells differentiate into neurons rather than glial cells. Thus, noggin acts to induce neuronal production through its suppression of endogenous bone morphogenic protein (Lim et al., "Noggin Antagonizes BMP Signaling To Create A Niche for Adult Neurogenesis," *Neuron* 28: 713-726 (2000); Zimmerman et al., "The Spemann Organizer Signal Noggin Binds and Inactivates Bone Morphogenetic Protein 4," *Cell* 86: 599-606 (1996), which are hereby incorporated by reference in their entirety). Therefore, the nucleic acid which encodes the neurotrophic factor noggin is suitable for use in the nucleic acid construct of the present invention.

An inhibitor of bone morphogenic proteins, like noggin, is capable of suppressing bone morphogenic protein, thereby driving the differentiation of progenitor cells in the brain into neurons. (Lim et al., "Noggin Antagonizes BMP Signaling To Create a Niche for Adult Neurogenesis," *Neuron* 28: 713-726 (2000); Zimmerman et al., "The Spemann Organizer Signal Noggin Binds and Inactivates Bone Morphogenetic Protein 4," *Cell* 86: 599-606 (1996), which are hereby incorporated by reference in their entirety). The suppression of bone morphogenic protein by noggin or noggin-like proteins, as they are also known, may be used effectively in combination with BDNF to further increase neuronal production in the brain.

A particularly suitable inhibitor of pro-gliogenic bone morphogenetic proteins is noggin with its heparin binding site removed. Instead of being administered as a nucleic acid construct encoding an inhibitor of pro-gliogenic bone morphogenetic proteins, the inhibitor can alternatively be provided in the form of a protein or polypeptide.

A gene or cDNA encoding the desired neurotrophic factor product or protein, or fragment thereof, may be obtained for example by screening a genomic or cDNA library, or by PCR amplification.

Providing a nucleic acid construct of the present invention involves incorporating the nucleic acid molecules of the present invention into host cells using conventional recombinant DNA technology. Generally, this involves inserting the nucleic acid molecule into an expression system to which the nucleic acid molecule is heterologous (i.e., not normally present). The heterologous nucleic acid molecule is inserted into the expression system which includes the necessary elements for the transcription and translation of the inserted protein coding sequences. The practice of the present invention will employ, unless otherwise indicated, conventional methods of virology, microbiology, molecular biology, and recombinant DNA techniques within the skill of the art. Such techniques are explained fully in the literature. See, e.g., Sambrook, et al., *Molecular Cloning: A Laboratory Manual* (1989); *DNA Cloning: A Practical Approach* vol. I & II (D. Glover, ed.); *Oligonucleotide Synthesis* (N. Gait, ed., Current Edition); *Nucleic Acid Hybridization* (B. Hames & S. Higgins, eds., Current Edition); *Fundamental Virology*, 2nd Edition, vol. I & II (B. N. Fields and D. M. Knipe, eds.), which are hereby incorporated by reference in their entirety.

The introduction of a particular foreign or native gene into a mammalian host is facilitated by first introducing the gene sequence into a suitable nucleic acid vector. "Vector" is used herein to mean any genetic element, such as a plasmid, phage, transposon, cosmid, chromosome, virus, virion, etc., which is capable of replication when associated with the proper control elements and which is capable of transferring gene sequences between cells. Thus, the term includes cloning and expression vectors, as well as viral vectors. The nucleic acid molecules of the present invention may be inserted into any of the many available expression vectors and cell systems using reagents that are well known in the art.

Examples of viruses which have been employed as vectors for the transduction and expression of exogenous genes in mammalian cells include the SV40 virus (Innis et al., "Chromatin Structure of Simian Virus 40-pBR322 Recombinant Plasmids in COS-1 Cells," *Mol. Cell Biol.* 3(12):2203-2210 (1983); Okayama et al., "Bacteriophage Lambda Vector for Transducing a cDNA Clone Library into Mammalian Cells," *Mol. Cell Biol.* 5(5):1136-1142 (1985), which are hereby incorporated by reference in their entirety) and bovine papilloma virus (Meneguzzi et al., "Plasmidial Maintenance in Rodent Fibroblasts of a BPV1-pBR322 Shuttle Vector Without Immediately Apparent Oncogenic Transformation of the Recipient Cells," *EMBO J.* 3(2):365-371 (1984); DiMaio et al., "Bovine Papillomavirus Vector that Propagates as a Plasmid in Both Mouse and Bacterial Cells," *Proc. Nat'l. Acad. Sci. USA* 79(13):4030-4034 (1982); Lusky et al., "Characterization of the Bovine Papilloma Virus Plasmid Maintenance Sequences," *Cell* 36(2):391-401 (1984); Giri et al., "Comparative Studies of the Expression of Linked *Escherichia coli* gpt Gene and BPV-1 DNAs in Transfected Cells," *Virology* 127(2):385-396 (1983), which are hereby incorporated by reference in their entirety), the retrovirus Moloney murine sarcoma virus (Perkins et al., "Design of a Retrovirus-Derived Vector for Expression and Transduction of Exogenous Genes in Mammalian Cells," *Mol. Cell Biol.* 3(6):1123-1132 (1983); Lee et al., "DNA Clone of Avian Fujinami Sarcoma Virus with Temperature-Sensitive Transforming Function in Mammalian Cells," *J. Virol.* 44(1):401-412 (1982); Curran et al., "FBJ Murine Osteosarcoma Virus: Identification and Molecular Cloning of Biologically Active Proviral DNA," *J. Virol.* 44(2):674-682 (1982); Gazit et al., "Mammalian Cell Transformation by a Murine Retrovirus Vector Containing the Avian Erythroblastosis Virus erbB Gene," *J. Virol.* 60(1): 19-28 (1986), which are hereby incorporated by reference in their entirety), and HIV-based viruses.

A number of adenovirus (Ad) based gene delivery systems have also been developed. Human adenoviruses are double-stranded DNA viruses which enter cells by receptor-mediated endocytosis. These viruses are particularly well suited for gene therapy, because they are easy to grow and manipulate and they exhibit a broad host range in vivo. Adenovirus is easily produced at high titers and is stable so that it can be purified and stored. Even in the replication-competent form-, adenoviruses generally cause only low level morbidity and are not associated with human malignancies. Furthermore, Ad infects both dividing and non-dividing cells; a number of tissues which are targets for gene therapy comprise largely non-dividing cells (U.S. Pat. No. 6,171,855 to Askari, which is hereby incorporated by reference in its entirety). For descriptions of various adenovirus-based gene delivery systems, see, e.g., Haj-Ahmad et al., "Development of a Helper-Independent Human Adenovirus Vector and Its Use in the Transfer of the Herpes Simplex Virus Thymidine Kinase Gene," *J. Virol.* 57(1):267-274 (1986); Bett et al., "Packaging Capacity and Stability of Human Adenovirus Type 5 Vectors," *J. Virol.* 67(10):5911-5921 (1993); Mittereder et al., "Evaluation of the Efficacy and Safety of in vitro, Adenovirus-Mediated Transfer of the Human Cystic Fibrosis Transmembrane Conductance Regulator cDNA," *Hum. Gene Ther.* 5(6): 717-729 (1994); Seth et al., "Mechanism of Enhancement of DNA Expression Consequent to Cointernalization of a Replication-Deficient Adenovirus and Unmodified Plasmid DNA," *J. Virol.* 68(2):933-940 (1994); Barr et al., "Efficient Catheter-Mediated Gene Transfer into the Heart Using Replication-Defective Adenovirus," *Gene Ther.* 1(1):51-58 (1994); Berkner et al., "Development of Adenovirus Vectors for the Expression of Heterologous Genes," *Biotechniques* 6(7):616-629 (1988); Rich et al., "Development and Analysis of Recombinant Adenoviruses for Gene Therapy of Cystic Fibrosis," *Hum. Gene Ther.* 4(4):461-476 (1993), which are hereby incorporated by reference in their entirety.

Retroviral vectors, capable of integration into the cellular chromosome, have also been used for the identification of developmentally important genes via insertional mutagenesis (see, e.g., U.S. Pat. No. 6,207,455 to Chang, which is hereby incorporated by reference in its entirety). Retroviral vectors are also used in therapeutic applications (e.g., gene therapy), in which a gene (or genes) is added to a cell to replace a missing or defective gene or to inactivate a pathogen such as a virus. The members of the family Retroviridae are characterized by the presence of reverse transcriptase in their virions (U.S. Pat. No. 6,207,344 to Chang, which is hereby incorporated by reference in its entirety). The family is divided into three subfamilies: (1) Oncovirinae, including all the oncogenic retroviruses, and several closely related non-oncogenic viruses; (2) Lentivirinae, the "slow retroviruses," discussed in greater detail below, and (3) Spumavirinae, the "foamy" retroviruses that induce persistent infections, generally without causing any clinical disease (U.S. Pat. No. 6,218,181 to Verma et al., which is hereby incorporated by reference in its entirety). Some of the retroviruses are oncogenic (i.e., tumorigenic), while others are not. The oncoviruses induce sarcomas, leukemias, lymphomas, and mammary carcinomas in susceptible species (U.S. Pat. No. 6,033,905 to Wilson et al., which is hereby incorporated by reference in its entirety). Retroviruses infect a wide variety of species, and may be transmitted both horizontally and vertically. They are integrated into the host DNA, and are capable of transmitting sequences of host DNA from cell to cell. This has led to the development of retroviruses as vectors for various purposes including gene therapy. For example, the majority of the approved gene transfer trials in the United States rely on replication-defective retroviral vectors harboring a therapeutic polynucleotide sequence as part of the retroviral genome (Miller et al., "Gene Transfer by Retrovirus Vectors Occurs Only in Cells that are Actively Replicating At The Time of Infection," *Mol. Cell Biol.* 10(8):4239-4442 (1990); Cometta et al., "No Retroviremia or Pathology in Long-term Follow-up of Monkeys Exposed to Amphotropic Retrovirus," *Hum. Gene Ther.* 2(3):215-219 (1991), which are hereby incorporated by reference in their entirety). As is known in the art, the major advantages of retroviral vectors for gene therapy are the high efficiency of gene transfer into certain types of replicating cells, the precise integration of the transferred genes into cellular DNA, and the lack of further spread of the sequences after gene transfer (U.S. Pat. No. 6,033,905 to Wilson et al., which is hereby incorporated by reference in its entirety).

As used herein, the term "lentivirus" refers to a group (or genus) of retroviruses that give rise to slowly developing disease. Viruses included within this group include HIV (human immunodeficiency virus; including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates. Diseases caused by these viruses are characterized by a long incubation period and protracted course. Usually, the viruses latently infect monocytes and macrophages, from which they spread to other cells. HIV, FIV, and SIV also readily infect T lymphocytes (i.e., T-cells). Lentivirus virions have bar-shaped nucleoids and contain genomes that are larger than other retroviruses. Lentiviruses use tRNA$^{lys}$ as primer for negative-strand synthesis, rather than the tRNA$^{pro}$ commonly used by other infectious mammalian retroviruses. The lentiviral genomes exhibit homology with each other, but not with other retroviruses (Davis et al., *Microbiology*, 4th ed., J. B. Lippincott Co., Philadelphia, Pa., pp. 1123-1151 (1990), which is hereby incorporated by reference in its entirety). An important factor in the disease caused by these viruses is the high mutability of the viral genome, which results in the production of mutants capable of evading the host immune response. The advantage of lentiviruses is the ability for sustained transgene expression. Thus, in one embodiment of the present invention, a lentiviral vector is employed to provide long-term expression of the neurotrophic transgene in a target cell.

Adeno-associated viruses (AAV) may also be employed as a vector in the present invention. AAV is a small, single-stranded (ss) DNA virus with a simple genomic organization (4.7 kb) that makes it an ideal substrate for genetic engineering. Two open reading frames encode a series of rep and cap polypeptides. Rep polypeptides (rep78, rep68, rep62, and rep40) are involved in replication, rescue, and integration of the AAV genome. The cap proteins (VP1, VP2, and VP3) form the virion capsid. Flanking the rep and cap open reading frames at the 5' and 3' ends are 145 bp inverted terminal repeats (ITRs), the first 125 bp of which are capable of forming Y- or T-shaped duplex structures. Of importance for the development of AAV vectors, the entire rep and cap domains can be excised and replaced with a therapeutic or reporter transgene (B. J. Carter, in "*Handbook of Parvoviruses*", ed., P. Tijsser, CRC Press, pp. 155-168 (1990), which is hereby incorporated by reference in its entirety). It has been shown that the ITRs represent the minimal sequence required for replication, rescue, packaging, and integration of the AAV genome (U.S. Pat. No. 5,871,982 to Wilson et al., which is hereby incorporated by reference in its entirety).

As noted above, viral vectors have been successfully employed in order to increase the efficiency of introducing a recombinant vector into suitably sensitive host cells. Therefore, viral vectors are particularly suited for use in the present invention, including any adenoviral (Ad), retroviral, lentiviral, or adeno-associated viral (AAV) vectors described above or known in the art. Current research in the field of viral vectors is producing improved viral vectors with high-titer and high-efficiency of transduction in mammalian cells (see, e.g., U.S. Pat. No. 6,218,187 to Finer et al., which is hereby incorporated by reference in its entirety). Such vectors are suitable in the present invention, as is any viral vector that comprises a combination of desirable elements derived from one or more of the viral vectors described herein. It is not intended that the expression vector be limited to a particular viral vector.

Certain "control elements" or "regulatory sequences" are also incorporated into the vector-construct. The term "control elements" refers collectively to promoter regions, polyadenylation signals, transcription termination sequences, upstream regulatory domains, origins of replication, internal ribosome entry sites ("IRES"), enhancers, and the like, which collectively provide for the replication, transcription, and translation of a coding sequence in a recipient cell. Not all of these control elements need always be present so long as the selected coding sequence is capable of being replicated, transcribed, and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcriptional control signals in eukaryotes comprise "promoter" and "enhancer" elements. Promoter and enhancer elements have been isolated from a variety of eukaryotic sources, including genes in yeast, insect, and mammalian cells, and viruses. Analogous control elements, i.e., promoters, are also found in prokaryotes. Such elements may vary in their strength and specificity. For example, promoters may be "constitutive" or "inducible."

A constitutive promoter is a promoter that directs expression of a gene throughout the development and life of an organism. Examples of some constitutive promoters that are widely used for inducing expression of transgenes include the nopoline synthase (NOS) gene promoter from *Agrobacterium tumefaciens* (U.S. Pat. No. 5,034,322 to Rogers et al., which is hereby incorporated by reference in its entirety), the cytomegalovirus (CMV) early promoter, those derived from any of the several actin genes, which are known to be expressed in most cells types (U.S. Pat. No. 6,002,068 to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, or a physiological stress directly imposed upon the organism such as cold, heat, toxins, or through the action of a pathogen or disease agent. A recombinant cell containing an inducible promoter may be exposed to an inducer by externally applying the inducer to the cell or organism by exposure to the appropriate environmental condition or the operative pathogen.

Inducible promoters may be used in the viral vectors of this invention. These promoters will initiate transcription only in the presence of an additional molecule. Examples of inducible promoters include the tetracycline response element and promoters derived from the β-interferon gene, heat shock gene, metallothionein gene or any obtainable from steroid hormone-responsive genes. Tissue specific expression has been well characterized in the field of gene expression and tissue specific and inducible promoters are well known in the art. These genes are used to regulate the expression of the foreign gene after it has been introduced into the target cell.

Another type of promoter suitable for the present invention is a cell specific promoter. "Specific," as used herein to describe a promoter, means that the promoter permits substantial transcription of the DNA only in a predetermined, or "chosen" cell type. A chosen cell type can refer to different types of cells, or different stages in the developmental cycle of a cell. An example of a cell specific promoter useful in the present invention is the nestin enhancer (E/nestin). This derives from the 637 bp-region between bases 1162 and 1798 of the second intronic enhancer of the rat nestin gene, which is evolutionarily conserved between human and rat. E/nestin is sufficient to control gene expression in CNS neuroepithelial progenitor cells (Lothian et al., "An Evolutionarily Conserved Region in the Second Intron of the Human Nestin Expression to CNS Progenitor Cells and to Early Neural Crest Cells," *Eur. J. Neurosci.* 9(3):452-462 (1997), Roy et al., "Promoter Targeted Selection and Isolation of Neural Progenitor Cells from Adult Human Ventricular Zone," *J. Neurosci. Research* 59: 321-331 (2000), which are hereby incorporated by reference in their entirety). In one aspect of the present invention, the nestin enhancer is placed upstream to a basal promoter in order to drive gene expression specifically in neural precursor cells. Another example of a cell specific promoter suitable for the present invention is the Tα1 tubulin promoter, which uses a regulatory sequence neuronal progenitor cell using a regulatory sequence expressed only in neuronal progenitor cells and young neurons (Roy et al., "In vitro Neurogenesis by Neural Progenitor Cells Isolated From the Adult Human Hippocampus," *Nature Medicine:* 6:271-277 (2000); (Wang et al., "Isolation of Neuronal Precursors by Sorting Embryonic Forebrain Transfected Regulated by the T Alpha 1 Tubulin Promoter," *Nat. Biotechnol.* 16(2): 196-201 (1998), which are hereby incorporated by reference in their entirety). Also suitable in the present invention are promoters of the musashi gene (Good et al., "The Human Musashi Homologue 1 (MSI1) Gene Encoding the Homologue of musashi/Nrp-1, A Neural RNA-Binding Protein Putatively Expressed in CNS Stem Cells And Neuroprogenitors Cells," *Genomics* 52:382-384 (1998), which is hereby incorporated by reference in its entirety), the SOX2 gene (Zapponi et al., "SOX2 Regulatory Sequences: Direct Expression of a β-geo Transgene to Telencephalic Neural Stem Cells and Precursors of Mouse Embryo Revealing Regionalization of Gene Expression in CNS Stem Cells," *Development* 127:2368-2382 (2000), which is hereby incorporated by reference in its entirety), and the neurogenin gene (Simmons, et al., "Neurogenin2 Expression in Ventral and Dorsal Spinal Neural Tube Progenitor Cells is Regulated by Distinct Enhancers," *Developmental Biol.* 229: 327-339 (2001), which is hereby incorporated by reference in its entirety), each of which is specific for neuroprogenitor cells at different stages of their development.

It will be appreciated by those skilled in the art that any number of suitable transcriptional regulatory elements may be used to direct specific cell-type gene expression the present invention. Selection will be highly dependent upon the vector system and host utilized.

Cell specific promoters are particularly preferable in the present invention, because they provide a second level of control over transgene expression, in addition to that of selective transduction by the vector. The most frequently used promoters are viral in origin, often derived from a different virus than the vector backbone, for example cytomegalovirus promoters have been used in all vector systems. Viral promoters have the advantages of being smaller, stronger, and better understood than most human promoter sequences.

To ensure efficient expression, 3' polyadenylation regions must be present to provide for proper maturation of the mRNA transcripts. The native 3'-untranslated region of the gene of interest is preferably used, but the polyadenylation signal from, for example, SV40, particularly including a splice site, which provides for more efficient expression, could also be used. Alternatively, the 3'-untranslated region derived from a gene highly expressed in a particular cell type could be fused with the gene of interest.

The vector of choice, a suitable marker gene, promoter/enhancer region(s), and an appropriate 3' regulatory region can be operably ligated together to produce the expression system of the present invention, or suitable fragments thereof, using well known molecular cloning techniques as described in Sambrook et al., *Molecular Cloning: A Laboratory Manual,* Second Edition, Cold Spring Harbor Press, NY (1989), and Ausubel et al. (1989) *Current Protocols in Molecular Biology,* John Wiley & Sons, New York, N.Y., which are hereby incorporated by reference in their entirety. The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner that a functional protein is produced.

Typically, an antibiotic or other compound useful for selective growth of the transformed cells only is added as a supplement to the media. The compound to be used will be dictated by the selectable marker element present in the plasmid with which the host cell was transformed. Suitable genes are those which confer resistance to gentamycin, G418, hygromycin, streptomycin, spectinomycin, tetracycline, chloramphenicol, and the like. Similarly, "reporter genes," which encode enzymes providing for production of an identifiable compound identifiable, or other markers which indicate relevant information regarding the outcome of gene delivery, are suitable. For example, various luminescent or phosphorescent reporter genes are also appropriate, such that the presence of the heterologous gene may be ascertained visually.

An example of a marker suitable for the present invention is the green fluorescent protein (GFP) gene. The isolated nucleic acid molecule encoding a green fluorescent protein can be deoxyribonucleic acid (DNA) or ribonucleic acid (RNA, including messenger RNA or mRNA), genomic or recombinant, biologically isolated or synthetic. The DNA molecule can be a cDNA molecule, which is a DNA copy of a messenger RNA (mRNA) encoding the GFP. In one embodiment, the GFP can be from *Aequorea victoria* (Prasher et al., "Primary Structure of the *Aequorea Victoria* Green-Fluorescent Protein," *Gene* 111(2):229-233 (1992); U.S. Pat. No. 5,491,084 to Chalfie et al., which are hereby incorporated by reference in their entirety). A plasmid encoding the GFP of *Aequorea victoria* is available from the ATCC as Accession No. 75547. Mutated forms of GFP that emit more strongly than the native protein, as well as forms of GFP amenable to stable translation in higher vertebrates, are commercially available from Clontech Laboratories, Inc. (Palo Alto, Calif.) and can be used for the same purpose. The plasmid designated pTα1-GFPh (ATCC Accession No. 98299) includes a humanized form of GFP. Indeed, any nucleic acid molecule encoding a fluorescent form of GFP can be used in accordance with the subject invention. Standard techniques are then used to place the nucleic acid molecule encoding GFP under the control of the chosen cell specific promoter.

Markers are also suitable for assessing neuronal production following injection. An exemplary marker for this purpose is the mitotic marker bromodeoxyuridine (BrdU). The subject can be injected with BrdU, which is indicative of DNA replication in cells, simultaneously or following the injection of the nucleic acid-viral vector of the present invention. Similarly, markers specific for neurogenesis, or neuronal production, can also be assessed in spinal cord by ELISA of the subject's CSF for the appropriate neurotrophic factor. Also suitable are markers which are indicative of the stage of development of a cell, for example, the NeuN gene, which is expressed only by mature neurons.

The selection marker employed will depend on the target species and/or host or packaging cell lines compatible with a chosen vector.

Once the nucleic acid construct of the present invention has been prepared and inserted into the desired vector, it is ready to be incorporated into a host cell. Basically, this method is carried out by transforming a host cell with a nucleic construct of the present invention under conditions effective to yield transcription of the DNA molecule in the host cell, using standard cloning procedures known in the art, such as that described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable hosts include, but are not limited to, bacteria, virus, yeast, mammalian cells, insect, plant, and the like. Where the vector is a viral vector, the host cell is chosen to optimize packaging, where required, and titer. For example, where the nucleic acid of the present invention is inserted into an adenovirus vector, the cell line HEK293 is an appropriate host line, with the expectation of high vector progeny titers. The vector DNA may be introduced into the packaging cell by any of a variety of transfection techniques, e.g., calcium phosphate coprecipitation, electroporation, etc. (See, e.g., Sambrook, et al., *Molecular Cloning: A Laboratory Manual* (1989); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Fundamental Virology*, 2nd Edition, vol. I & II (B. N. Fields and D. M. Knipe, eds.), which are hereby incorporated by reference in their entirety). Other conventional methods employed in this invention include homologous recombination of the viral genomes, plaquing of viruses in agar overlay, methods of measuring signal generation, and the like known in the art or described in literature.

Following transfection of an appropriate host with the viral vector of the present invention, the virus is propagated in the host and collected. Generally, this involves collecting the cell supernatants at periodic intervals, and purifying the viral plaques from the crude lysate, using techniques well-known in the art, for example, cesium chloride density gradient. The titer (pfu/ml) of the virus is determined, and can be adjusted up (by filtration, for example), or down (by dilution with an appropriate buffer/medium), as needed. In the present invention, typical Ad titers are in the range of $10^{10}$-$10^{12}$ pfu/ml.

To effect the gene therapy aspect of the present invention, the isolated, purified viral vector-containing the neurotrophin-encoding nucleic acid is injected into a subject's lateral ventricles or ventricular zone wall under conditions effective to express the neurotrophic factor and to induce neuronal production in the subject. "Subject" is meant herein to include any member of the class Mammalia including, without limitation, humans and nonhuman primates, such as chimpanzees and other apes and monkey species; farm animals including cattle, sheep, pigs, goats and horses; domestic animals including cats and dogs; laboratory animals including rodents such as mice rats, and guinea pigs, and the like. The term does not denote a particular age or sex. Thus, adults and post-natal (newborn) subjects, as well as fetuses, are intended to be covered.

The recombinant viruses of the present invention may be administered to a subject, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The recombinant viruses of this invention may be administered in sufficient amounts to transfect the desired cells and provide sufficient levels of integration and expression of the selected transgene to provide a therapeutic benefit without undue adverse effects or with medically acceptable physiological effects which can be determined by those skilled in the medical arts. While the preferable route of injection is the region of the lateral ventricle and ventricular wall zone of the subject's brain, other conventional and pharmaceutically acceptable parenteral routes of administration include direct delivery to the target organ, tissue or site, intranasal, intravenous, intramuscular, subcutaneous, intradermal, and oral administration are encompassed by the present invention.

Dosages of the recombinant virus will depend primarily on factors, such as the condition being treated, the selected gene, the age, weight, and health of the patient, and may thus vary among patients. A therapeutically effective human dosage of the viruses of the present invention is believed to be in the range of about 100 microliters to 10 milliliters of saline solution containing concentrations of from about $2.5 \times 10^{10}$ pfu/ml to $2.5 \times 10^{12}$ pfu/ml virus of the present invention. Effective dosage for a given species can be determined by correcting for differences in surface area of the ventricular wall, the volume of ventricular cerebrosphinal fluid (CSF), and body weight. The dosage will be adjusted to balance the therapeutic benefit against any viral toxicity or side effects. The levels of expression of the selected gene can be monitored to determine the selection, adjustment, or frequency of dosage administration.

Another aspect of the present invention relates to a method of recruiting neurons to a subject's brain. This embodiment of the present invention comprises providing a neurotrophic factor and providing an inhibitor of pro-gliogenic bone morphogenetic proteins. The neurotrophic factor and the inhibitor are then administered into the subject's lateral ventricles or ventricular zone wall under conditions effective to recruit neurons to the brain of the subject.

The neurotrophic factor and the an inhibitor of pro-gliogenic bone morphogenetic proteins are both formulated and administered in the form of proteins or nucleic acid constructs encoding such proteins, as described above. Preparation of the DNA construct can be carried out as described above. Suitable nucleic acids include the neurotrophins given above, and viral propagation and injection are as described above. The present invention provides a method of recruiting neurons to the brain which is superior to those currently existing in the art and results in the recruitment of neurons to the olfactory bulb, the basal ganglia of the brain, the caudate nucleus, the putamen, and/or the globus pallidus, as well as to the to the cortex of a subject's brain.

A further aspect of the present invention relates to a method of treating a neurodegenerative condition by providing a neurotrophic factor and an inhibitor of pro-gliogenic bone morphogenetic proteins. The neurotrophic factor and the inhibitor are administered into the subject's lateral ventricles or ventricular zone wall under conditions effective to treat a neurodegenerative condition. The neurotrophic factor and the an inhibitor of pro-gliogenic bone morphogenetic proteins are both formulated and administered in the form of proteins or nucleic acid constructs encoding such proteins, as described above.

The neurodegenerative condition treated in accordance with this aspect of the present invention can be Huntington's Disease, Parkinson's Disease, amyotrophic lateral sclerosis, multiple sclerosis, stroke, and/or traumatic injury to the brain and spinal cord.

Huntington's Disease (HD) is an autosomal dominant neurodegenerative disease characterized by a relentlessly progressive movement disorder with devastating psychiatric and cognitive deterioration. HD is associated with a consistent and severe atrophy of the neostriatum which is related to a marked loss of the GABAergic medium-sized spiny projection neurons, the major output neurons of the striatum. The intraventricular injections of BDNF DNA in a viral vector results in a distinct population of newly generated neurons in the neostriatum, indicating that the neurotrophic factor BDNF is particularly useful as a potential treatment for HD. Direct injection of BDNF also would be useful in treating Huntington's Disease.

Another embodiment of the present invention relates to a method of suppressing astrocyte generation and inducing neuronal production in a subject. In this method, an inhibitor of pro-gliogenic bone morphogenetic proteins is provided and the inhibitor is administered into the subject's lateral ventricles or ventricular zone wall under conditions effective to suppress astrocyte generation and induce neuronal production in the brain and spinal cord of the subject.

The inhibitor of pro-gliogenic bone morphogenetic proteins is formulated and administered in the form of a protein or nucleic acid construct encoding such protein, as described above.

A further aspect of the present invention pertains to a method of treating a neurologic condition in a subject. This method includes providing an inhibitor of pro-gliogenic bone morphogenetic proteins and administering the inhibitor to the subject's lateral ventricles, ventricular wall, or site of injury under conditions effective to treat a neurologic condition. The neurologic condition can be Huntington's Disease, Parkinson's Disease, amyotrophic lateral sclerosis, multiple sclerosis, stroke, a condition mediated by glial scar formation, or traumatic injury to the brain or spinal cord.

The inhibitor of pro-gliogenic bone morphogenetic proteins is formulated and administered in the form of a protein or nucleic acid construct encoding such protein, as described above.

Another aspect of the present invention relates to a method of suppressing glial scar formation in a subject. This method involves providing an inhibitor of progliogenic bone morphogenetic proteins. The inhibitor of progliogenic bone morphogenic proteins is administered to the subject's ventricles, ventricular wall, or sites of injury at risk for glial scar formation under conditions effective to suppress glial scar formation in the subject.

This inhibitor of pro-gliogenic bone morphogenic proteins is formulated and administered in the form of a protein or nucleic acid construct encoding such protein, as described above.

The present invention also relates to a method of introducing a therapeutic protein into a subject's brain and spinal cord. In this method, a nucleic acid molecule encoding the therapeutic protein is introduced into the subject's ependyma. The protein from the nucleic acid molecule is then expressed within the subject's ependyma, and the expressed protein is permitted to migrate within the subject's brain and spinal cord.

The protein or polypeptide can be formulated and administered in the form of a nucleic acid construct encoding the protein or polypeptide, as described above.

In all aspects of the present invention, the injection of a neurotrophic factor encoding nucleic acid or bone morphogenetic protein encoding nucleic acid into the subependyma, the cellular layer lining the ventricular cavities of the adult brain, is intended to activate and mobilize endogenous neuroprogenitor cells of the diseased or injured brain and spinal cord in order to restore lost brain cells. The resulting production of new neurons and the recruitment of new neurons to regions of the brain, such as the striatum and the cortex, suggest that neuronal populations may be replaceable in the brain and spinal cord of subjects suffering from neurodegenerative diseases including, but not limited to, Huntington's Disease, Parkinson's Disease, amyotrophic lateral sclerosis, and multiple sclerosis, as well as in victims of neurological damage due to stroke or traumatic injury to the brain and/or spinal cord.

In all aspects of the present invention, the injection of a neurotrophic factor encoding nucleic acid into the subependyma, the cellular layer lining the ventricular cavities of the adult brain, is intended to activate and mobilize endogenous neuroprogenitor cells of the diseased or injured brain and spinal cord in order to restore lost brain cells. The resulting production of new neurons and the recruitment of new neurons to regions of the brain, such as the striatum and the cortex, suggest that neuronal populations may be replaceable in the brain and spinal cord of subjects suffering from neurodegenerative diseases including, but not limited to, Huntington's Disease, Parkinson's Disease, amyotrophic lateral sclerosis, and multiple sclerosis, as well as in victims of neurological damage due to stroke or traumatic injury to the brain and/or spinal cord.

EXAMPLES

Example 1

Adenovirus Construction

Replication-incompetent AdBDNF and AdNull were constructed and raised as previously described (Benraiss et al., *J Neurosci* 21:6718-31 (2001), which is hereby incorporated by reference). Using the same previously described techniques (Benraiss et al., *J Neurosci* 21:6718-31 (2001); Bajocchi et al., *Nature Genetics* 3:229-234 (1993); and Graham et al., In *Methods in Molecular Biology*, ed. Murray, E. (Humana, pp. 109-128 (1991), which are hereby incorporated by reference in their entirety), a $\Delta$E1 type 5 adenovirus was made to encode, under CMV control, human noggin$^{\Delta B2}$, from which the B2 heparin binding domain had been deleted, yielding AdNoggin$^{\Delta B2}$ (Paine-Saunders et al., *J. Biol. Chem* (2001) and Economides et al., Moraga, Calif. (2000), which are hereby incorporated by reference in their entirety).

Example 2

Experimental Design and Sterotaxic Injection

In the first set of experiments, six adult Sprague-Dawley rats received bilateral 3 µl intraventricular injections (Benraiss et al., *J Neurosci* 21:6718-31 (2001) and Paxinos et al., *The Rat Brain in Stereotaxic Coordinates* (Academic, Orlando, Fla.) (1986), which is hereby incorporated reference in their entirety) of AdNoggin$^{\Delta B2}$ (n=3) or AdNull (n=3). Both viruses were titered to 2.5×1010 pfu/ml. In the second set of experiments, AdNoggin$^{\Delta B2}$ and AdBDNF were both brought to a titer of 2.5×10$^{10}$ pfu/ml within the same solution, and 3 µl of this cocktail were injected intraventricularly (n=3). Matched controls received AdNull (n=3). The rats were then given 18 daily i.p. injections of bromodeoxyuridine (BrdU; 100 mg/kg). On day 20 or 56, animals were sacrificed, CSF withdrawn and brains processed as previously described (Benraiss et al., *J Neurosci* 21:6718-31 (2001), which is hereby incorporated by reference in its entirety). Additionally, a cohort of animals which received intraventricular AdBDNF or AdNull (n=3/group) followed by 18 daily injections of BrdU, were secondarily injected on day 42 with 1 µl of 2% Fluorogold (Biotium, Hayward, Calif.), injected bilaterally into the globus pallidus. The injected animals were sacrificed a week later, perfused with 2% paraformnaldehyde, and their brains processed for BrdU immunolabeling followed by confocal identification of BrdU+/Fluorogold-tagged striatal cells.

Example 3

ELISA

Noggin levels in the CSF were determined with a two site ELISA using two rat-derived anti-human noggin monoclonal antibodies. Coat Antibody RP57-16, which binds at the N-terminal half of noggin, was coated at 2 µg/ml in PBS, followed by an incubation with 10 mg/ml BSA solution in PBS for 2 hours to block any free protein-binding sites. On the ELISA plate, serial 2-fold dilutions of a known concentration of noggin protein were performed in triplicate, and CSF samples were added. 100 µl of a 1 µg/ml solution of the anti-noggin biotinylated monoclonal RP57-21-biotin, which binds to the cysteine-rich domain of noggin, were added to each well. To detect RP57-21-biotin the plates were then incubated with a streptavidin-HRP conjugate (Life Technologies) at a 1:5000 dilution, for 1 hour.

Example 4

In situ Hybridization

Noggin RNA probes were made from pBlue.mNOG. This DNA plasmid was linearized with BamH1 for the sense control probe or with Not1 for the antisense probe, and in vitro transcribed with T3 RNA polymerase for the sense probe and T7 RNA polymerase for the antisense probe. The probes were radioactively labeled with S35-UTP. In situ hybridization was then performed on 15 µm sagittal brain sections of AdNoggin$\Delta$B2 (n=3) or AdNull (n=3)-injected animals, as previously described (Valenzuela et al., *Neuron* 10:963-974 (1993), which is hereby incorporated by reference in its entirety).

Example 5

Immunochemistry and Quantification

Sagittal 15 µm sections were stained for BrdU and neuronal/glial markers using double-immunofluorescence, as previously described (Benraiss et al., *J Neurosci* 21:6718-31 (2001) and Roy et al., *J Neurosci* 19:9986-95 (1999), which are hereby incorporated by reference in their entirety). All secondary antibodies (Molecular Probes) were pre-absorbed against to avoid nonspecific staining.

Striatal BrdU+ cells counts were done on eleven 15 µm sagittal sections per animal; every 16th section was analyzed at 240 µm intervals. The striatal region sampled began with the first appearance of striatal fascicles, and proceeded 2.6 mm laterally. The number of striatal BrdU+/βIII-tubulin+ cells/mm3 in a given section was determined by multiplying the percentage of BrdU+ cells determined by confocal microscopy to express βIII-tubulin (see below), by the mean number of BrdU+ cells/mm2. All comparisons were done by Student's two-tailed t test.

Example 6

Confocal Imaging

In sections double-stained for BrdU and βIII-tubulin, dopamine-and cAMP-regulated phosphoprotein (DARPP- 32), glutamic acid decarboxylase (GAD)67, S100β or GFAP, or in Fluorogold-injected animals immunostained for BrdU alone, single striatal BrdU+ cells were randomly selected for confocal imaging. Using an Olympus Fluoview confocal microscope, images were acquired in both red and green emission channels using an argon-krypton laser, and were analyzed as previously described (Benraiss et al., *J Neurosci* 21:6718-31 (2001), which is hereby incorporated by reference in its entirety). Fluorogold images were thresholded and pseudocolored as light rather than dark blue so as to increase visual contrast.

Example 7

Intraventricular AdNogginΔB2 Yields High-Level Noggin Expression by the Ventricular Wall Noggin overexpression was achieved via transduction of the ventricular wall with a recombinant adenovirus encoding human noggin. In order to ensure widespread local availability of the vector-encoded noggin, a ΔB2 noggin mutein was used, from which the heparin binding site was deleted to permit sustained solubility of secreted noggin (Paine-Saunders et al., *J. Biol. Chem* (2001), which is hereby incorporated by reference in its entirety). To assess the production of noggin by this vector, in situ hybridization was used to visualize noggin expression in both normal controls, and in rats treated with adenoviral noggin. To this end, 6 adult rats were injected with either AdNoggin$^{\Delta B2}$ or AdNull, and sacrificed 3 weeks later. Their brains were sectioned sagitally at 15 μm and subjected to in situ hybridization for noggin mRNA, using S35-UTP-labeled probes for mouse noggin. Endogenous noggin expression was seen in the septum and olfactory bulb, as well as the dentate gyrus and CA1-3 of the hippocampus in both the AdNoggin$^{\Delta B2}$-and AdNull-injected animals. Significant periventricular noggin, however, was only seen in animals that received AdNogginΔB2 (FIG. 3).

Next, an ELISA was used to ask if AdNoggin$^{\Delta B2}$ injection raised noggin protein levels in the CSF. To this end, ventricular CSF was withdrawn by cisterna magna puncture, 3 weeks after virus injection. In the AdNoggin$^{\Delta B2}$-injected animals (n=3), ELISA revealed that CSF noggin averaged 52.0±4.5 ng/ml, or 42.9±7.2 μg/g protein (mean±SE). In contrast, noggin was undetectable in the CSF of AdNull-injected animals (n=3) (p<0.0001 by paired t-test) (FIG. 4).

Example 8

Noggin Overexpression Suppressed Gliogenesis by the Adult Ventricular Zone

Applicants previously noted that AdBDNF induced heterotopic neuronal addition to the neostriatum (Benraiss et al., *J Neurosci* 21:6718-31 (2001), which is hereby incorporated by reference in its entirety). Unlike the olfactory subependyma of the anterior subventricular zone and rostral migratory stream, whose precursor cells are largely committed to neuronal phenotype, the striatal subependyma includes a mixed population of multipotential stem cells and both neuronal and glial progenitors, and hence generates both neuronal and glial daughter cells. On this basis, it was postulated that if noggin could suppress glial differentiation of striatal SZ daughter cells, then AdNoggin infection might be associated with a lower incidence of BrdU-labeled SZ astrocytes, as defined by the incidence of BrdU+/GFAP+ and BrdU+/S100β+ subependymal cells. To this end, the incidence of both BrdU+, GFAP+/BrdU+ and S100β+/BrdU+ cells in the subventricular zones of both AdNull and AdNoggin-treated rats was scored, at their respective 3 week survival points.

It was found that in the forebrain, the AdNoggin-injected rats exhibited substantial suppression of subependymal glial differentiation, as manifested by 80-90% reductions in both GFAP+/BrdU+ and S100β+/BrdU+ subependymal astrocytes. Specifically, whereas 46.8±5.8% of BrdU+SZ cells in AdNull-injected animals expressed GFAP, only 5.7±1.1% of BrdU+SZ cells were GFAP+ in AdNoggin-injected animals (p<0.001). Furthermore, whereas 39.9±0.5% of BrdU+SZ cells in AdNull-injected animals expressed glial S100 β$^+$ only 6.8±0.9% of BrdU+SZ cells were S100β$^+$ in AdNoggin-injected animals (p<0.001). The marked reduction in the proportion of GFAP+ and S100 β$^+$ cells among BrdU-incorporating SZ cells was noted even though the incidence of SZ BrdU labeling was not significantly different between AdNoggin- and AdNull-injected rats (FIG. 5). These data indicated that noggin overexpression was sufficient to reduce glial production by SZ progenitor cells.

It was next asked if progenitors of the striatal SZ responded differently to AdNoggin than did progenitors of the fimbrial and callosal SZ (designated together as the white matter SZ). For this purpose, sagittal sections were taken that spanned the mediolateral extent of the striatum (L1.9-L3.9); these were divided into rostral (striatal) and dorsal/caudal (white matter) segments (Paxinos et al., *The Rat Brain in Stereotaxic Coordinates* (Academic, Orlando, Fla.) (1986), which is hereby incorporated by reference). In the white matter SZ of AdNull-injected animals, 64.9±8.1% of all BrdU+ cells were GFAP+, and 49.9±4.9% expressed S100β. In contrast, only 7.6±0.4% of BrdU+ cells were GFAP+ and 8.8±0.3% S100 β$^+$ in AdNoggin-injected animals (p<0.001 for each marker, by paired t tests). Similarly, in the AdNull striatal SZ, 38.0±4.7% of BrdU+ cells were GFAP+, and 28.3±2.6% S100β+ in AdNull-injected animals, whereas only 3.1±1.9% were GFAP+ and 6.4±1.1% S100 β$^+$ in their AdNoggin-injected counterparts (p<0.001) (FIG. 5). These data confirmed that AdNoggin significantly decreased the proportion of GFAP+-S100β+ astrocytes arising from SZ progenitor cells, and did so across all SZ regions scored.

Example 9

AdNoggin and AdBDNF Synergistically Increased Neuronal Addition to the Neostriatum It was next postulated that by virtue of its suppression of gliogenesis, noggin overexpression might make more ventricular zone progenitors cells responsive to neuronal instruction by BDNF. As such, noggin and BDNF co-overexpression might be expected to provide a concurrently permissive and instructive environment for striatal neurogenesis. This postulate was tested in 250 g normal Sprague-Dawley rats, that were injected once intraventricularly with both AdBDNF and AdNoggin, then injected daily for 3 weeks thereafter with BrdU (FIG. 1). The animals were then sacrificed, their brains cut sagitally at 15 μm, and the sections double-immunostained for βIII-tubulin and BrdU, and scored as described (Benraiss et al., *J. Neurosci* 21:6718-31 (2001), which is hereby incorporated by reference in its entirety).

It was found that the AdNoggin-treated animals had an average of 1163±157 BrdU+ cells/mm3 in their striata (FIG. 6). Among a randomly chosen sample of 414 BrdU+ striatal cells located in sections (n=40) selected at random from 3 AdNoggin-treated brains, 21 cells were confirmed as labeled for both BrdU and βIII-tubulin by confocal imaging. Thus, 5.1±1.3% (=21/414) of the BrdU+ cells in the AdNoggin-treated rat striata, or 59 cells/mm$^3$, were neurons. This was not significantly different than AdNull-injected animals, in which 2.4±1.5% of the BrdU+ cells were neurons. Thus, noggin alone had no discernible effect upon striatal neuronal addition.

In contrast, the concurrent use of AdBDNF and AdNoggin greatly enhanced neuronal addition to the striatum. Whereas the AdNull-injected rats exhibited an average of 1103±367 BrdU+ striatal cells/mm$^3$, the AdNoggin/AdBDNF-treated animals showed a marginal and statistically insignificant increment in striatal BrdU+ cells to 2522±557/mm$^3$ (p=0.15 by paired t-test). Strikingly though, whereas relatively few of these cells were confirmed as neuronal in AdNull animals, among a random sample of 458 BrdU+ striatal cells derived from 3 AdNoggin/AdBDNF brains, 61 cells (13.3±3.9%) were found by confocal imaging to be double-labeled for BrdU and βIII-tubulin. Thus, almost 14% of the BrdU+ cells in the AdNoggin/AdBDNF-treated striata were neurons. On this basis, it was estimated that at least 335 new neurons/mm$^3$ (13.3% of 2522 BrdU+ cells/mm$^3$) may be added to the rat striatum within 3 weeks of AdNoggin/AdBDNF infection. This greatly exceeded the rare striatal neuronal addition noted in AdNull-injected rats, in which only 2.4±1.5% of BrdU+ cells, or 26/mm$^3$, were βIII-tubulin+ (p<0.02). In addition, AdNoggin/AdBDNF-treated animals showed a significant increment in striatal neuronal addition when compared with animals treated with AdBDNF alone (p<0.05). Moreover, the AdNoggin-treated animals showed no significant increment in striatal neuronal addition relative to their AdNull controls. Since the AdNoggin-treated animals showed no significant striatal neuronal addition, while the AdBDNF-treated animals did, and since the AdBDNF/AdNoggin-treated animals exhibited significantly more neuronal recruitment than the BDNF-treated rats, it is concluded that the effect of BDNF and noggin together was synergistic. These data are consistent with the notion that AdNoggin treatment results in an expansion of the progenitor pool without any specific increment in neuronal differentiation, and that BDNF then acts to induce neuronal differentiation from the noggin-expanded pool of competent progenitors. When administered together, BDNF and noggin thereby cooperate to induce neuronal recruitment to the neostriatum.

Example 10

AdBDNF/AdNogginΔB2-Induced Neurons Survived Striatal Integration

By 8 weeks after viral infection, and 5 weeks after the cessation of BrdU injection, the AdNoggin/AdBDNF-treated animals retained an average of 1986±185 BrdU+ striatal cells/mm3, compared to 1351±65 BrdU+ striatal cells/mm$^3$ noted in AdNull-injected controls (p<0.02 by paired t-test). Among 142 BrdU+ striatal cells selected at random from 3 AdNoggin/AdBDNF-treated brains, 15 cells (10.5±3.5%) were identified by confocal analysis as BrdU+/βIII-tubulin+. Even at this late time point, an average of 208 new striatal neurons/mm$^3$ remain in AdNoggin/AdBDNF co-injected animals, significantly more (p<0.05) than AdNull-injected animals, in whom only 0.6±0.6% of BrdU+ cells, or 8 cells/mm$^3$ fulfilled applicants antigenic criteria for neuronal designation (FIG. 6). Taken together, these data indicate that newly generated, AdNoggin/AdBDNF-induced neurons survive in the adult neostriatum, long after their mitotic generation and initial parenchymal recruitment.

Example 11

AdBDNF/AdNoggin-Induced Striatal Neurons Differentiated into Medium Spiny Cells

Applicants had previously noted that AdBDNF-induced striatal neurons express markers characteristic of medium spiny neurons, such as DARRP-32, calbindin and glutamic acid decarboxylase (GAD67), an enzyme involved in the synthesis of GABA from glutamate (Benraiss et al., *J Neurosci* 21:6718-31 (2001) and Ivkovic et al., *J. Neurosci.* 19:5409-5419 (1999), which are hereby incorporated by reference in their entirety). To determine if AdBDNF/AdNoggin-induced cells likewise differentiated as GABAergic neurons, sections taken from animals sacrificed at 3 weeks were immunolabeled for BrdU and GAD67 or DARPP-32. It was found that 8.5% of the imaged BrdU+ cells (11/130) co-expressed GAD67+, while 7.9% of the imaged BrdU+ cells (15/189) co-expressed DARPP-32 (FIG. 7). This compared to the 13.7±3.9% of striatal BrdU+ cells that were antigenically defined as neurons, by virtue of their co-expression of βIII-tubulin. In fact, the ratio of GAD67+/BrdU+ cells to total βIII-tubulin+/BrdU+ cells in the AdBDNF/AdNoggin-treated animals (62%) was similar to that which previously noted in animals treated with AdBDNF alone (58%) (Benraiss et al., *J Neurosci* 21:6718-31 (2001), which is hereby incorporated by reference in its entirety). These data suggest that most AdBDNF/AdNoggin-induced striatal cells matured as GABAergic medium spiny neurons.

Example 12

Newly Generated Striatal Neurons Developed Projections to the Globus Pallidus

It was next asked whether the new, BDNF/noggin-induced neurons of the rat caudate-putamen were processed to their normal developmental target, the globus pallidus. To address this question, retrograde tracer Fluorogold was injected into the globus pallidus of rats injected with AdBDNF 6 weeks earlier, who had been given daily BrdU injections for the first 18 days after viral injection (FIG. 2). A week after Fluorogold delivery, the rats were sacrificed and their striata assessed for the incidence of BrdU+/Fluorogold+ cells, which were thereby defined as newly generated pal lidal projection neurons. It was found that 4.0±2.3% of striatal BrdU+ cells in AdBDNF-injected animals, or 59 cells/mm$^3$, projected to the globus pallidus. These data suggest that roughly 40% of the 143±26 newly generated neurons/mm$^3$ induced by AdBDNF in the striatum send long-distance projections to the globus pallidus by 7 weeks after viral injection, or within the 4-7 weeks following their mitogenesis (FIG. 8). Since the globus pallidus is the major target of caudate-putaminal medium spiny axons, these results suggest that newly-generated medium spiny neurons can project axons to appropriate postsynaptic targets. Most strikingly, these observations argue that the noggin/BDNF-triggered induction of endogenous progenitor cells may be sufficient to initiate this process in the adult forebrain.

These results indicate that the concurrent overexpression of noggin and BDNF may be used to stimulate and direct neuronal production from endogenous progenitor cells in the adult mammalian neostriatum. This strategy of using noggin to suppress glial lineage, while simultaneously using BDNF to direct the neuronal differentiation of SZ progenitors, yielded a markedly synergistic induction of both neostriatal neurogenesis and parenchymal recruitment. By inhibiting SZ progenitor glial differentiation, noggin may have increased the pool of progenitor cells potentially responsive to BDNF; together the two clearly exercised a synergistic effect on neuronal recruitment to the striatum. Interestingly though, whereas glial differentiation was suppressed in AdNoggin-injected animals throughout the entire lateral ventricular wall, the combination of AdBDNF and AdNoggin resulted in heterotopic neuronal addition only to the striatum, and not to the neocortex or septum. The regionally-restricted nature of noggin-accentuated neurogenesis argues that glial suppression may be necessary, but not sufficient, for inducing neurogenesis in otherwise non-neurogenic regions of the adult central nervous system. In addition, endogenous noggin is expressed not only in neurogenic areas like the olfactory bulb and dentate gyrus, but also in the non-neurogenic septum (Mehler et al., *Int J Dev Neurosci* 13:213-40 (1995), which is hereby incorporated by reference) (see also FIG. 3), again suggesting that noggin expression alone is not sufficient for neuronal production and recruitment in vivo. Rather, noggin appears to be an important contributor, whose relative importance in a given brain region is likely a function not only of the levels and species of endogenous pro-gliogenic BMPs, but also of the responsiveness of the resident progenitor population. Together, these findings argue strongly that other locally-active and regionally-restricted factors delimit neuronal production and recruitment in the adult forebrain.

The generation of new striatal neurons was followed in these animals by their parenchymal survival and integration. The cells scored at 3 weeks largely remained at 8 weeks, such that no appreciable loss of the newly generated striatal cohort was noted during this period. Remarkably, Fluorogold backfills revealed that by 7 weeks after viral injection, a large proportion of the newly generated, BrdU+ striatal neurons had extended fibers to their usual target, the globus pallidus. These fibers traversed a distance of just over 2 mm, typical for the striatopallidal projection in rats. The long-distance extension of fibers from new projection neurons to distant nuclear targets has rarely been demonstrated in the adult central nervous system, and never before in uninjured mammals. A testosterone-mediated process of fiber extension from the principal vocal control nucleus to its motor target nucleus has been demonstrated in normal adult songbirds, and the current findings would appear conceptually analogous to this process, in that each of these instances of adult-derived axogenic neurons have been newly generated (Alvarez-Buylla et al., *J. Neuroscience* 33:585-601 (1997), which is hereby incorporated by reference). A similar instance of long distance fiber extension has also been reported by new neurons in the injured rat neocortex, following local compensatory neurogenesis (Magavi et al., *Nature* 405:951-955 (2000), which is hereby incorporated by reference). These disparate examples of axogenesis by newly generated neurons in the adult CNS indicate not only that newly generated striatal neurons can generate projection fibers, but also that that the regional environment may retain the local developmental cues that direct axonal extension to appropriate targets. Together, these data argue that neurons induced from resident progenitor cells might be capable of at least limited tract regeneration in the adult forebrain.

These results indicate that the concurrent suppression of glial differentiation by noggin, and promotion of neuronal differentiation by BDNF, is an effective strategy for mobilizing endogenous progenitor cells in the adult forebrain. These cells may be thereby stimulated to achieve the quantitatively significant addition of new neurons to the adult neostriatum, a region that otherwise does not recruit new neurons in postnatal or adult animals. The differentiation of these new striatal cells as GABAergic DARPP-32$^+$ neurons, the long-distance projection of these new neurons to the globus pallidus, and the survival of these cells for at least 2 months after their genesis, all suggest their ability to mature, function and survive in the adult forebrain. The induced production of these cells by a strategy of concurrent glial suppression and neuronal induction thereby suggests a means by which phenotypically-appropriate neurons might be regenerated from endogenous progenitor cells, in sufficient numbers to restore those medium spiny cells lost to Huntington's Disease.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed:

1. A method of suppressing gliogenesis in a mammalian subject comprising:

providing a nucleic acid construct encoding an inhibitor of pro-gliogenic bone morphogenic proteins, wherein said inhibitor is noggin with its heparin binding site removed, and administering the inhibitor directly into the mammalian subject's lateral ventricles or ventricular wall under conditions effective to suppress gliogenesis in the brain and spinal cord of the mammalian subject.

2. The method according to claim 1, wherein the nucleic acid construct is in a viral vector.

3. The method according to claim 2, wherein the viral vector is an adenoviral vector, a lentiviral vector, a retroviral vector, an adeno-associated viral vector, or a combination thereof.

4. The method according to claim 1, wherein the nucleic acid construct further comprises a constitutive promoter for controlling expression of the inhibitor.

5. The method according to claim 1, wherein the nucleic acid construct further comprises a cell-specific promoter for controlling expression of the inhibitor.

6. The method according to claim 1, wherein the nucleic acid construct farther comprises an inducible or conditional promotor for controlling expression of the inhibitor.

7. A method of treating a human subject having a neurologic condition comprising:

providing a nucleic acid construct encoding an inhibitor of pro-gliogenic bone morphogenic proteins, wherein said inhibitor is noggin with its heparin binding site removed, and administering the inhibitor directly to the human subject's lateral ventricles, ventricular wall, or site of injury under conditions effective to suppress gliogenesis, thereby treating the neurologic condition, wherein the neurologic condition is selected from the group consisting of Huntington's Disease, multiple sclerosis, stroke, a condition mediated or exacerbated by glial scar formation, and traumatic injury to the brain and spinal cord.

8. The method according to claim 7, wherein the neurologic condition is Huntington's Disease.

9. The method according to claim 7, wherein the neurologic condition is or results from traumatic brain injury.

10. The method according to claim 7, wherein the neurologic condition is or results from traumatic spinal cord injury.

11. The method according to claim 7, wherein the neurologic condition is stroke.

12. The method according to claim 7, wherein the neurologic condition is a condition mediated or exacerbated by glial scar formation.

13. The method according to claim 7, wherein the nucleic acid construct is in a viral vector.

14. The method according to claim 13, wherein the viral vector is an adenoviral vector, a lentiviral vector, a retroviral vector, an adeno-associated viral vector, or a combination thereof.

15. The method according to claim 7, wherein the nucleic acid construct further comprises a constitutive promoter for controlling expression of the inhibitor.

16. The method according to claim 7, wherein the nucleic acid construct further comprises a cell-specific promoter for controlling expression of the inhibitor.

17. The method according to claim 7, wherein the nucleic acid construct further comprises an inducible or conditional promotor for controlling expression of the inhibitor.

18. A method of suppressing glial scar formation in a mammalian subject comprising:
providing a nucleic acid construct encoding an inhibitor of progliogenic bone morphogenic proteins, wherein said inhibitor is noggin with its heparin binding site removed, and
administering the inhibitor of progliogenic bone morphogenic proteins directly to the mammalian subject's ventricles, ventricular wall, or sites of injury at risk for glial scar formation under conditions effective to suppress glial scar formation in the mammalian subject.

19. The method according to claim 18, wherein the nucleic acid construct is in a viral vector.

20. The method according to claim 19, wherein the viral vector is an adenoviral vector, a lentiviral vector, a retroviral vector, an adeno-associated viral vector, or a combination thereof.

21. The method according to claim 18, wherein the nucleic acid construct comprises a constitutive promoter for controlling expression of the inhibitor.

22. The method according to claim 18, wherein the nucleic acid construct further comprises a cell-specific promoter for controlling expression of the inhibitor.

23. The method according to claim 18, wherein the nucleic acid construct further comprises an inducible or conditional promoter for controlling expression of the inhibitor.

24. The method of claim 1, wherein the subject is human.

25. The method of claim 7, wherein the subject is human.

26. The method of claim 18, wherein the subject is human.

* * * * *

UNITED STATES PATENT AND TRADEMARK OFFICE
CERTIFICATE OF CORRECTION

PATENT NO. : 7,576,065 B2  Page 1 of 1
APPLICATION NO. : 10/368809
DATED : August 18, 2009
INVENTOR(S) : Goldman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 315 days.

Signed and Sealed this

Seventh Day of September, 2010

David J. Kappos
*Director of the United States Patent and Trademark Office*